United States Patent
Liu et al.

(10) Patent No.: US 9,145,462 B2
(45) Date of Patent: Sep. 29, 2015

(54) GLIOBLASTOMA MULTIFORME-REACTIVE ANTIBODIES AND METHODS OF USE THEREOF

(75) Inventors: Bin Liu, Hercules, CA (US); James D. Marks, Kensington, CA (US); Xiaodong Zhu, San Francisco, CA (US); Scott Bidlingmaier, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1102 days.

(21) Appl. No.: 13/172,759

(22) Filed: Jun. 29, 2011

(65) Prior Publication Data
US 2012/0039915 A1  Feb. 16, 2012

Related U.S. Application Data

(60) Provisional application No. 61/360,394, filed on Jun. 30, 2010.

(51) Int. Cl.
| | | |
|---|---|---|
| *A61K 39/395* | (2006.01) | |
| *C07K 16/28* | (2006.01) | |
| *C07K 16/30* | (2006.01) | |
| *C12N 5/095* | (2010.01) | |
| *G01N 33/574* | (2006.01) | |

(52) U.S. Cl.
CPC ......... *C07K 16/2896* (2013.01); *C07K 16/3053* (2013.01); *C12N 5/0695* (2013.01); *G01N 33/57407* (2013.01); *H05K 999/00* (2013.01); *C07K 2317/21* (2013.01); *C07K 2317/622* (2013.01); *C07K 2317/73* (2013.01); *C07K 2317/77* (2013.01); *C07K 2317/92* (2013.01)

(58) Field of Classification Search
None
See application file for complete search history.

(56) References Cited

PUBLICATIONS

White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
Bidlingmaier et al. (2008). "The utility and limitations of glycosylated human CD133 epitopes in defining cancer stem cells," J Mol Med (Berl). 86(9):1025-32.
Zhu et al. (2010). "Identification of internalizing human single-chain antibodies targeting brain tumor sphere cells," Mol Cancer Ther. 9(7):2131-41.

* cited by examiner

*Primary Examiner* — Laura B Goddard
*Assistant Examiner* — Meera Natarajan
(74) *Attorney, Agent, or Firm* — Morrison & Foerster LLP

(57) ABSTRACT

The present disclosure is generally related to antibodies that bind specifically to glioblastoma multiforme (GBM) cells. In particular, the present disclosure provides compositions comprising human single chain or full-length antibodies that bind tumor cells. Additionally the present disclosure provides methods of using the anti-GBM antibodies.

22 Claims, 18 Drawing Sheets

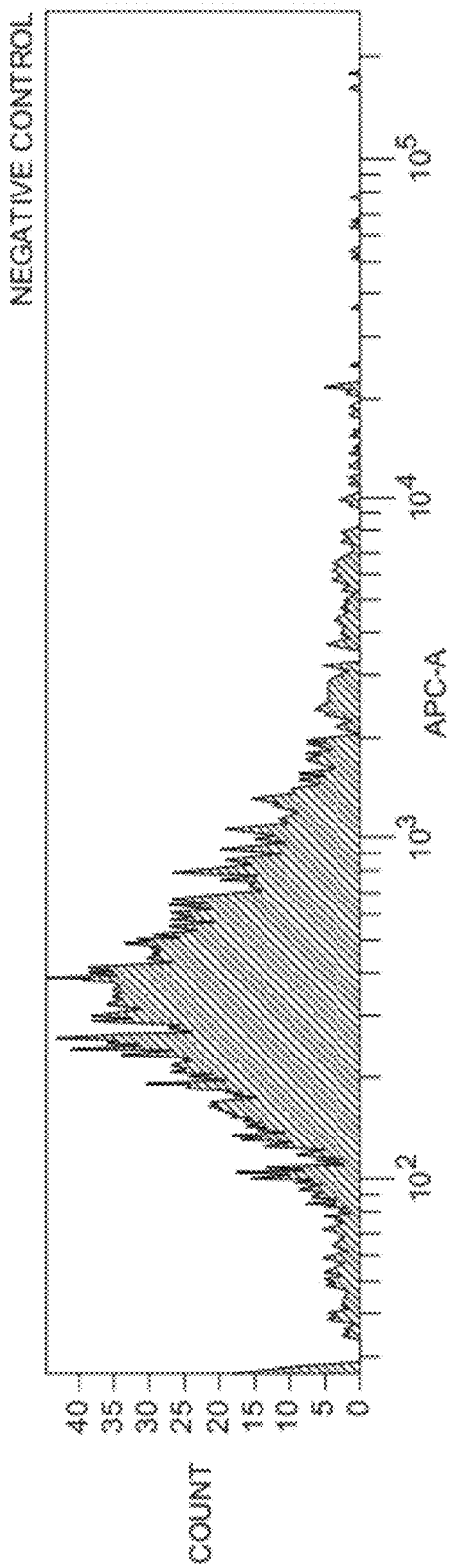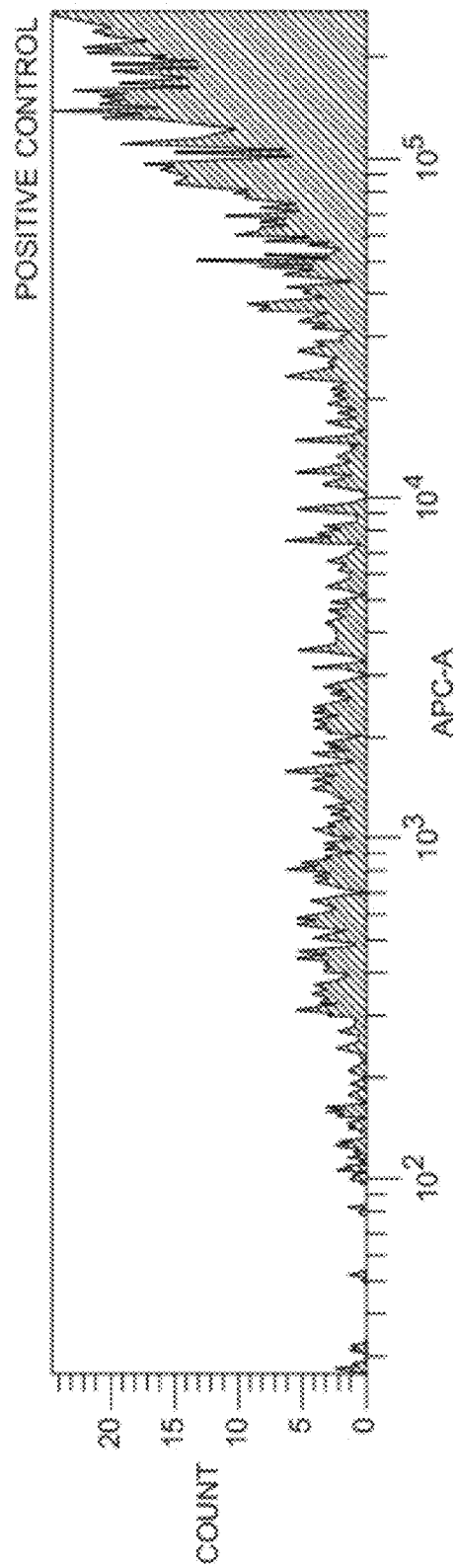

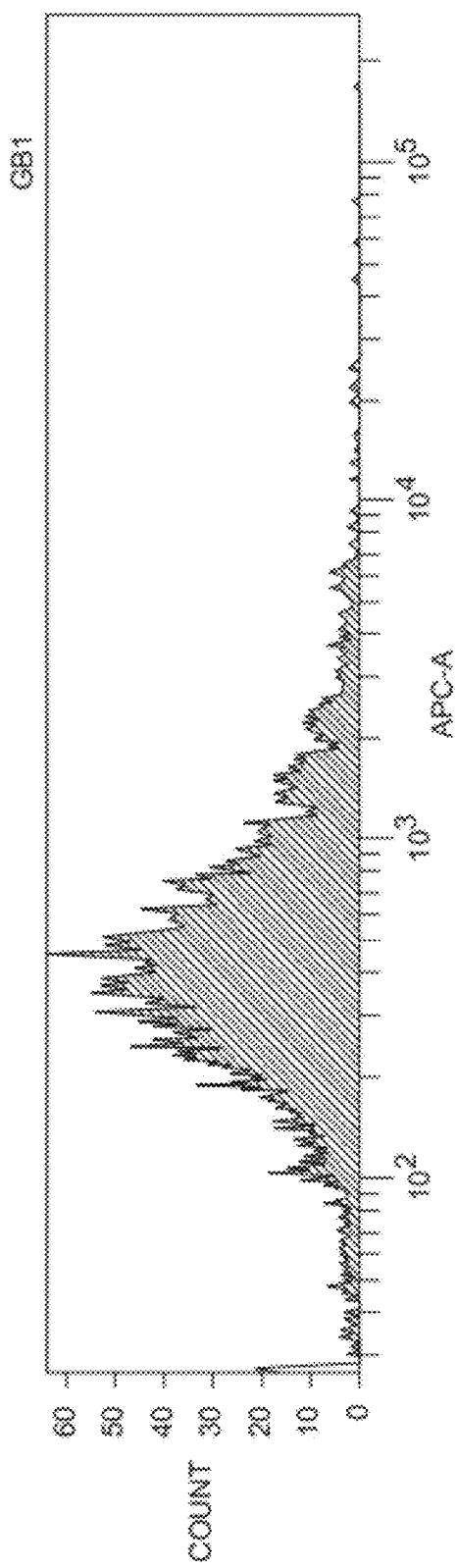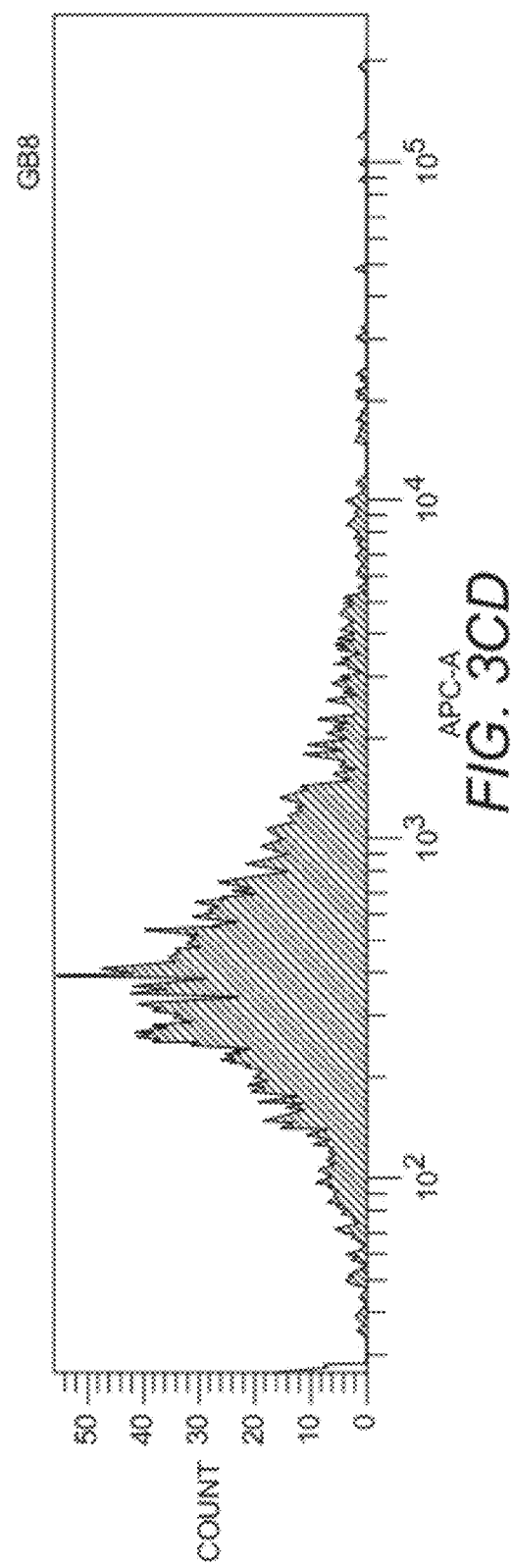

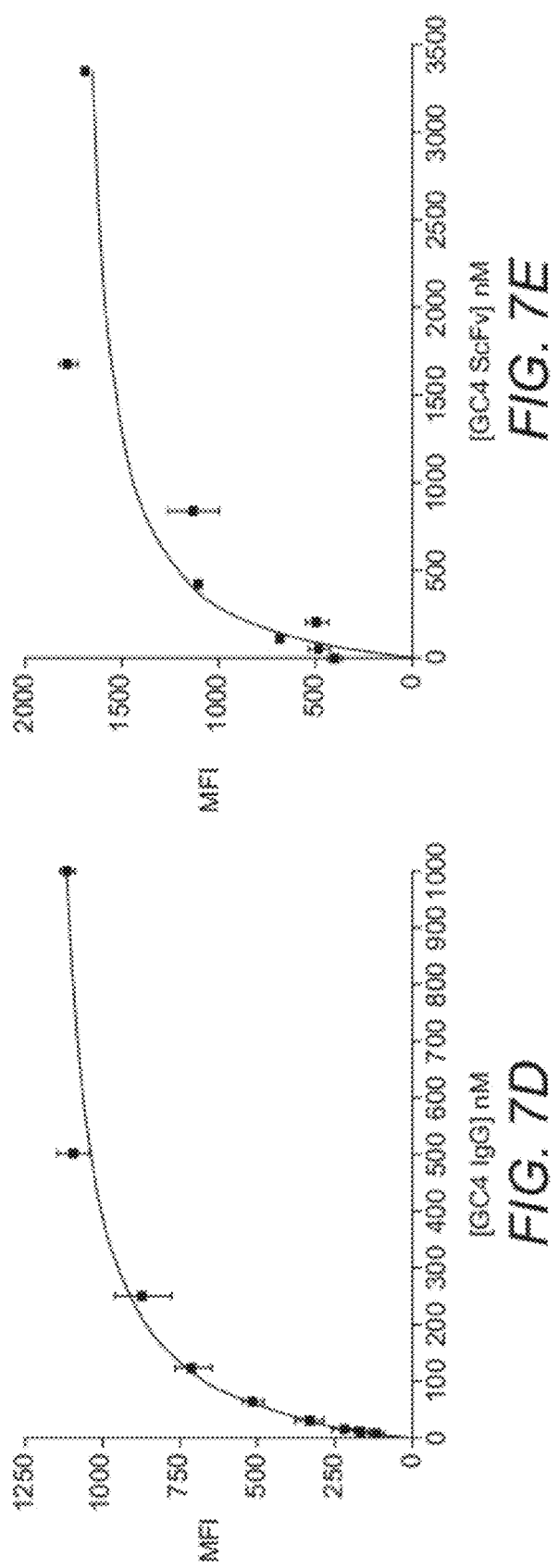

US 9,145,462 B2

GLIOBLASTOMA MULTIFORME-REACTIVE ANTIBODIES AND METHODS OF USE THEREOF

CROSS-REFERENCE TO RELATED APPLICATION

This application claims the benefit under 35 USC 119(e) of U.S. Provisional Patent Application No. 61/360,394, filed Jun. 30, 2010, which is incorporated herein by reference in its entirety for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 643662001400SeqList.txt, date recorded: Oct. 24, 2011, size: 28 KB).

STATEMENT REGARDING FEDERALLY SPONSORED RESEARCH OR DEVELOPMENT

This invention was made with government support under RO1 CA118919 and P50 CA097257 awarded by the National Institutes of Health. The government has certain rights in the invention.

FIELD

The present disclosure is generally related to antibodies that bind specifically to glioblastoma multiforme (GBM) cells. In particular, the present disclosure provides compositions comprising human single chain or full-length antibodies that bind tumor cells. Additionally the present disclosure provides methods of using the anti-GBM antibodies.

BACKGROUND

Glioblastoma multiforme (GBM) is the most common and aggressive form of primary brain tumor, accounting for 52% of all primary brain tumor cases and 20% of all intracranial tumors. The median survival time for a newly diagnosed patient is approximately one year (Krex et al., Brain, 130: 2596-606, 2007). Current methods of treatment involve chemotherapy, radiotherapy, and/or surgery, all of which are palliative measures that are not curative (Nicholas, Expert Rev Anticancer Ther, 7:S23-7, 2007; Benitez et al., Curr Med Chem, 15:729-42, 2008; Chang et al., Clin Adv Hematol Oncol, 5:894-902, 2007; and Reardon et al., Curr Treat Options Oncol, 9:1-22, 2008). One problem with current treatment methods is that even with complete gross surgical resection of the tumor combined with the best available treatment, recurrence of the tumor is nearly impossible to prevent, and consequently the long-term survival rate for GBM patients is extremely low.

It has been hypothesized that tumors are heterogeneous and only some of the tumor cells with stem-like properties are able to initiate and sustain tumor development (Reya et al., Nature, 414:105-11, 2001; Pardal et al., Nat Rev Cancer, 3:895-902, 2003; and Dalerba et al, Annu Rev Med, 58:267-84, 2007). It has been further postulated that current therapies targeting the bulk tumor are unable to completely eliminate these tumor-initiating subpopulations, leading to tumor recurrence and treatment failure (Eyler and Rich, J Clin Oncol, 26:2839-45, 2008; and Jiang et al., Leukemia, 21:926-35, 2007). Therapies optimized for eliminating these subpopulations would therefore be more effective in preventing recurrence than those targeting the bulk tumor (Eyler and Rich, J Clin Oncol, 26:2839-45, 2008; and Sims et al., Nat Clin Pract Oncol, 4:516-25, 2007). While conceptually appealing, therapies that target these tumor-initiating cells have yet to be developed for use in clinical practice.

Tumor-initiating cells were initially identified in hematological malignancies and later in many types of solid tumors, including brain tumors. A subpopulation of cells that are positive for the glycosylation-dependent conformational CD133 epitopes (AC133 and/or AC141) have been identified in malignant gliomas, and this subpopulation has been shown to have significantly enhanced potency for initiating tumors in immunocompromised mice (Singh et al., Cancer Res, 63:5821-8, 2003; Singh et al., Oncogene, 23:7267-73, 2004; Singh et al., Nature, 432:396-401, 2004; Yuan et al., Oncogene, 23:9392-400, 2004; and Bidlingmaier et al., J Mol Med, 86:1025-32, 2008). In one study, as few as 100 CD133 epitope-positive human glioma cells were shown to be capable of tumor initiation in immunocompromised mice, whereas 100,000 CD133 epitope-negative cells isolated from the same tumor mass were non-tumorigenic (Singh et al., Nature, 432:396-401, 2004).

Thus, a significant biomedical need exists for compositions that target GBM tumor-initiating cells.

SUMMARY

The present disclosure relates to isolated antibodies or fragments thereof that specifically bind to glioblastoma multiforme (GBM) tumor-initiating cells and methods of producing and using the isolated anti-GBM antibodies. The isolated antibodies or fragments thereof of the present disclosure find use in diagnostic and therapeutic applications.

In particular, the disclosure provides isolated antibodies that binds specifically to glioblastoma multiforme (GBM) tumor sphere cells, wherein the anti-GBM antibody comprises an antigen binding site that comprises: (a) a heavy chain comprising (i) complementarity determining region (CDR)-H1 comprising SEQ ID NO: 2, (ii) CDR-H2 comprising SEQ ID NO: 4, and (iii) CDR-H3 comprising SEQ ID NO: 6, and a light chain comprising (iv) CDR-L1 comprising SEQ ID NO: 34, (v) CDR-L2 comprising SEQ ID NO: 36, and (vi) CDR-L3 comprising SEQ ID NO: 38; (b) a heavy chain comprising (i) complementarity determining region (CDR)-H1 comprising SEQ ID NO: 10, (ii) CDR-H2 comprising SEQ ID NO: 12, and (iii) CDR-H3 comprising SEQ ID NO: 14, and a light chain comprising (iv) CDR-L1 comprising SEQ ID NO: 42, (v) CDR-L2 comprising SEQ ID NO: 44, and (vi) CDR-L3 comprising SEQ ID NO: 46; (c) a heavy chain comprising (i) complementarity determining region (CDR)-H1 comprising SEQ ID NO: 18, (ii) CDR-H2 comprising SEQ ID NO: 20, and (iii) CDR-H3 comprising SEQ ID NO: 22, and a light chain comprising (iv) CDR-L1 comprising SEQ ID NO: 50, (v) CDR-L2 comprising SEQ ID NO: 52, and (vi) CDR-L3 comprising SEQ ID NO: 54; (d) a heavy chain comprising (i) complementarity determining region (CDR)-H1 comprising SEQ ID NO: 26, (ii) CDR-H2 comprising SEQ ID NO: 28, and (iii) CDR-H3 comprising SEQ ID NO: 30, and a light chain comprising (iv) CDR-L1 comprising SEQ ID NO: 58, (v) CDR-L2 comprising SEQ ID NO: 60, and (vi) CDR-L3 comprising SEQ ID NO: 62; or (e) a heavy chain comprising (i) complementarity determining region (CDR)-H1 comprising SEQ ID NO: 67, (ii) CDR-H2 comprising SEQ ID NO: 69, and (iii) CDR-H3 comprising SEQ ID NO: 71, and a light chain comprising (iv) CDR-L1 comprising SEQ ID NO: 75, (v) CDR-L2 comprising SEQ ID NO: 77, and (vi) CDR-L3 comprising SEQ ID NO: 79. In some embodiments the antigen binding site comprises the heavy chain variable region of SEQ ID NO: 8, and the light chain variable region of SEQ ID NO: 40; the heavy chain variable region of SEQ ID NO: 16, and the light chain variable region of SEQ ID NO: 48; the heavy chain variable region of SEQ ID NO: 24, and the light chain variable region of SEQ ID NO: 56; the heavy chain variable region of SEQ ID NO: 32, and the light chain variable region of SEQ ID NO: 64; or the heavy chain variable region of SEQ ID NO: 73, and the light chain variable region of SEQ ID NO: 81. In some embodiments, the present disclosure provides an isolated anti-GBM antibody that competes for binding to glioblastoma multiforme (GBM) tumor sphere cells with the anti-GBM antibody selected from the group consisting of GC4, GB1, GB8, GH9 and GPD32. In some preferred embodiments, the antibody inhibits self-renewal of GBM tumor sphere cells and/or inhibits proliferation of GBM tumor sphere cells. In some embodiments, the GBM tumor sphere cells comprise GBM tumor-initiating cells. In some embodiments, the antibody is an antibody fragment. In some embodiments, the fragment is an Fab, F(ab')$_2$, Fv or Sfv fragment. In other embodiments, the antibody is a full-length human immunoglobulin g (IgG) antibody. In some embodiments, the antibody is coupled to one of the group consisting of a detectable marker, a toxin, and a chemotherapeutic agent. In some embodiments, the detectable marker is one of the group consisting of a radioisotope, a metal chelator, an enzyme, a fluorescent compound, a bioluminescent compound, and a chemiluminescent compound. In some embodiments, the radioisotope comprises one of the group consisting of $^{212}$Bi, $^{131}$I, $^{131}$In, $^{90}$Y, $^{186}$Re, $^{211}$At, $^{125}$I, $^{188}$Re, $^{153}$Sm, $^{213}$Bi, $^{32}$P, and $^{177}$Lu. In some embodiments, the toxin comprises one of the group consisting of ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha sarcin, gelonin, mitogellin, retstrictocin, phenomycin, enomycin, curicin, crotin, calicheamicin, sapaonaria officinalis inhibitor, glucocorticoid, auristatin, auromycin, yttrium, bismuth, combrestatin, duocarmycins, dolostatin, cc 1065, and cisplatin. In addition, the present disclosure provides isolated nucleic acids encoding the anti-GBM antibody. In some embodiments, the present disclosure provides an expression vector comprising the nucleic acid in operable combination with a regulatory sequence. The present disclosure also provides host cells comprising the expression vector.

In further embodiments, the present disclosure provides methods for characterizing a biopsy sample from a patient, comprising: a) contacting the sample with the anti-GBM antibody; and b) detecting the binding of the anti-GBM antibody to cells of the sample. In some embodiments, the biopsy sample is from a brain tumor.

Moreover, the present disclosure provides methods for treating a cancer patient, comprising: a) providing a composition comprising the anti-GBM antibody; and b) administering to the patient the composition in an amount effective to inhibit proliferation of tumor cells of the patient. In some embodiments, the tumor cells are glioblastoma multiforme (GBM) tumor cells. In some embodiments, the composition is administered intravenously or intracranially. Some methods of the present disclosure further comprise administering an effective amount of an additional chemotherapeutic agent to the patient. In some embodiments, the methods further comprise one or both of surgically resecting the tumor cells and administering radiation therapy.

BRIEF DESCRIPTION OF THE DRAWINGS

FIG. 2 depicts the selection of phage antibodies binding to the CD133+ cell population.

FIG. 3 depicts the results of co-expression of the CD133 epitope and phage-bound antigens.

FIG. 5A shows the internalization of Q-dot 655-labeled GC4 scFv by GBM tumor sphere cells. Representative images are shown for each indicated incubation condition. Control: GBM sphere cells incubated with Q-dot 655-labeled control non-binding scFv (N3M2). This non-binding scFv was originally picked from the unselected naïve library and has been used as a negative control in our previous studies (25, 50). Scale bar, 2 µm. FIG. 5B depicts the quantification of percent internalized. Following incubation with phage antibodies, data from two time points (1 h and 4 h) were collected and analyzed. Surface-bound phage antibodies were removed by washing with a low pH glycine buffer. The percentage of internalized phage is calculated based on the ratio of internalized over total cell associated phage antibodies. The experiments were done in triplicates. Error bars indicate standard deviations.

FIG. 6A shows GC4 but not other GBM tumor sphere cell-binding scFvs significantly inhibited GBM sphere cell proliferation. Cloning efficiencies were calculated from tumor spheres formed per 1,000 GBM cells seeded. Control, untreated sphere cells. N3M2, a non-binding scFv control. Experiments were done in triplicates with standard deviations indicated by error bars. *, $P<0.05$ for pairs indicated. FIG. 6B depicts the inhibition of established GBM tumor spheres by GC4. Established spheroids were treated with a control non-binding scFv and the GC4 scFv. The number of spheroids exceeding 50 μm in diameter was counted and indicated. *, $P<0.05$.

FIG. 7D shows that binding constant of GC4 IgG1 to GBM tumor spheres. Measured at RT by FACS, the kd of the GC4 IgG is 79.69 nM, with standard deviation of 9.20 nM. MFI values were fitted using GraphPad. FIG. 7E depicts the binding constant of GC4 scFv to GBM tumor spheres. Measured at RT by FACS, the kd of the GC4 scFv is 222.22 nM, with standard deviation of 82.22 nM. MFI values were fitted using GraphPad.

DEFINITIONS

Figure 1A:
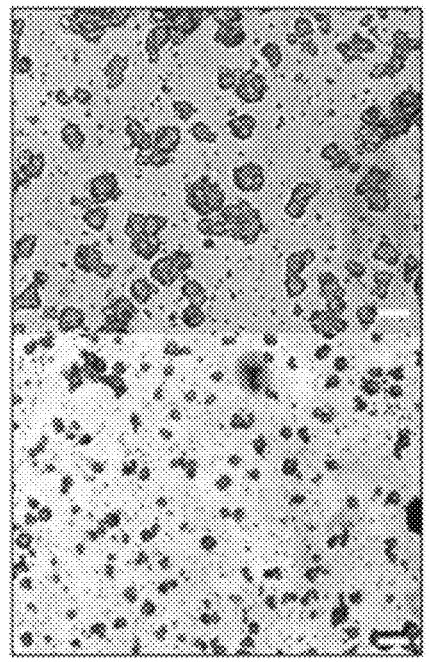
FIG. 1A depicts the morphology of GBM tumor spheres derived from xenografts and fresh human tissues after 14 days of incubation in serum free restrictive media. Scale bar, 500 µm.

To facilitate an understanding of the embodiments disclosed herein, a number of terms and phrases are defined below.

As used herein, "GBM tumor-initiating cells" refers to stem cell-like glioblastoma multiforme cells that are able to initiate and sustain GBM tumor development. An example of GBM tumor-initiating cells are GBM cells that are positive for the glycosylation-dependent conformational CD133 epitopes (AC133 and/or AC141). GBM tumor spheres and GBM tumor sphere cells comprise GBM tumor-initiating cells.

As used herein, an intact "antibody" comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcRη) and the first component (C1q) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989 Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv or scFv (See e.g., Bird et al., Science 242:423 426, 1988; and Huston et al., Proc Natl Acad Sci USA, 85:5879-5883, 1988). Such single chain antibodies are included by reference to the term "antibody" Fragments can be prepared by recombinant techniques or enzymatic or chemical cleavage of intact antibodies.

The terms "single-chain Fv" or "scFv" as used herein, refer to antibody fragments that contain the VH and VL domains of an antibody, where these domains are present in a single polypeptide chain. Preferably, the Fv polypeptide further contains a polypeptide linker between the VH and VL domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "complementarity determining region" or "CDR" as used herein, refers to a region within an antibody where the region complements an antigen's shape. Thus, a CDR determines the antibody's affinity and specificity for a specific antigen. The CDR is the most variable part of the antibody, and contributes to antibody diversity, allowing the antibody to recognize a vast repertoire of antigens.

An "isolated" antibody or immunoglobulin, as used herein, refers to an antibody or immunoglobulin that is substantially free of other components in which such antibodies or immunoglobulin are naturally found. Moreover, an isolated antibody or immunoglobulin may be substantially free of other cellular material and/or chemicals.

The term "human sequence antibody" or "human antibody" includes antibodies having variable and constant regions (if present) derived from human immunoglobulin sequences. The human sequence antibodies of the disclosure may include amino acid residues not encoded by human germline immunoglobulin sequences (e.g., mutations introduced by random or site-specific mutagenesis in vitro or by somatic mutation in vivo). However, the term "human sequence antibody", as used herein, is not intended to include antibodies in which entire CDR sequences sufficient to confer antigen specificity and derived from the germline of another mammalian species, such as a mouse, have been grafted onto human framework sequences (i.e., humanized antibodies). The human sequence antibodies of the disclosure can be produced in a non-human transgenic mammal, e.g., a transgenic mouse, capable of producing multiple isotypes of human (e.g., monoclonal or polyclonal) antibodies (e.g., IgM, IgD, IgG, IgA and/or IgE) to a variety of antigens by undergoing V-D-J recombination and, for non IgM/non IgD antibodies, isotype switching. Accordingly, various aspects of the disclosure include antibodies and antibody fragments, and pharmaceutical compositions thereof, as well as non-human transgenic mammals, and B-cells and hybridomas for making such monoclonal antibodies.

The term "recombinant human antibody", as used herein, includes all human sequence antibodies of the disclosure that are prepared, expressed, created or isolated by recombinant means, such as antibodies isolated from an animal (e.g., a mouse) that is transgenic for human immunoglobulin genes (described further below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "antigen" refers to any substance capable, under appropriate conditions, of inducing a specific immune response and reacting with the products of that response (e.g., specific antibody and/or specifically sensitized T lymphocytes). The disclosure provides human sequence antibodies to antigens, such as GBM tumor-inducing cells and primary GBM cells. Antibodies of the present disclosure include antibodies that may mediate molecular and/or cellular effector functions such as complement lysis, phagocytosis, or killing by natural killer cells; and antibodies that block or antagonize signals transduced by cell surface receptors. Some of these antibodies can bind to an epitope on a human receptor so as to inhibit the receptor from interacting with a ligand or co-receptor.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art.

"Specific binding" refers to preferential binding of an antibody to a specified antigen relative to other non-specified antigens. The phrase "specifically (or selectively) binds" to an antibody refers to a binding reaction that is determinative of the presence of the protein in a heterogeneous population of proteins and other biologics. Typically, the antibody binds with a dissociation constant ($K_D$) of about $1 \times 10^{-7}$ M or less, more preferably about $1 \times 10^{-8}$ M or less and even more preferably $1 \times 10^{-9}$ M or less, and binds to the specified antigen with an affinity that is at least two-fold greater than its affinity for binding to a non-specific antigen (e.g., BSA, KLH, casein) other than the specified antigen or a closely-related antigen. The phrases "an antibody recognizing an antigen" and "an antibody specific for an antigen" are used interchangeably herein with the term "an antibody that binds specifically to an antigen". A predetermined antigen is an antigen that is chosen prior to the selection of an antibody that binds to that antigen.

The phrase "specifically bind(s)" or "bind(s) specifically" when referring to an antibody which has intermediate or high binding affinity, exclusively or predominately, to a target antigen. The phrase "specifically binds to" refers to a binding reaction which is determinative of the presence of a target antigen in the presence of a heterogeneous population of antigens. Thus, under designated assay conditions, the specified binding moieties bind preferentially to a particular target antigen and do not bind in a significant amount to other components present in a test sample. A variety of assay formats may be used to select antibodies that are specifically reactive with a particular antigen. For example, solid-phase ELISA immunoassays, immunoprecipitation, surface plasmon resonance, and Western blot are used to identify antibodies that specifically react with the antigen. Typically a specific or selective reaction will be at least twice background signal or noise and more typically more than 10 fold background signal.

Except when noted, the terms "patient" or "subject" are used interchangeably and refer to mammals such as human patients and non-human primates, as well as experimental animals such as rabbits, rats, and mice, and other animals.

The term "treating" includes the administration of the compounds or agents of the present disclosure to prevent or delay the onset of the symptoms, complications, or biochemical indicia of a disease, alleviating the symptoms or arresting or inhibiting further development of the disease, condition, or disorder (e.g., brain tumors). Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. Optimized expression of these sequences in other eukaryotic cells is also envisioned herein. The amino acid sequences encoded by optimized nucleotide sequences are also referred to as optimized.

The term "substantially pure" or "isolated" means an object species (e.g. an antibody of the disclosure) has been identified and separated and/or recovered from a component of its environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the disclosure) can also be purified to essential homogeneity (contaminant species cannot be detected in the composition by conventional detection methods) wherein the composition consists essentially of derivatives of a single macromolecular species. For example, an isolated antibody to a human antigen can be substantially free of other antibodies that do not bind to the human antigen of interest (e.g., bind to a different antigen). Further, an isolated antibody that specifically binds to an epitope, isoform or variant of human antigen may, however, have cross-reactivity to other related antigens, e.g., from other species (e.g., species homologs). Moreover, an isolated antibody of the disclosure may be substantially free of other cellular material (e.g., non-immunoglobulin associated proteins) and/or chemicals.

The terms "nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides. The term "isolated nucleic acid" in reference to nucleic acids encoding antibodies or antibody portions (e.g., VH, VL, CDR3) that bind to the antigen, is intended to refer to a nucleic acid in which the nucleotide sequences encoding the antibody or antibody portion are free of other nucleotide sequences encoding antibodies or antibody portions that bind antigens other than the antigen of interest (other sequences may naturally flank the nucleic acid in human genomic DNA).

The term "substantially identical," in the context of two nucleic acids or polypeptides refers to two or more sequences or subsequences that have at least about 80%, about 85%, about 90%, about 95% or higher nucleotide or amino acid residue identity, when compared and aligned for maximum correspondence, as measured using the following sequence comparison method and/or by visual inspection. Such "substantially identical" sequences are typically considered to be homologous. The "substantial identity" can exist over a region of sequence that is at least about 10 residues, about 15 residues, about 20 residues, about 25 residues, about 30 residues, about 35 residues, about 40 residues, about 45 residues, or about 50 residues in length, over a region of at least about 25 residues, over a region of at least about 50 residues, over a region of at least about 75 residues, over a region of at least about 100 residues, over a region of at least about 125 residues, or over a region at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention. An alternative structural definition has been proposed (Chothia et al., J Mol Biol, 196:901-917, 1987; Chothia et al., Nature 342:878-883, 1989; and Chothia et al., J Mol Biol, 186:651-663, 1989).

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the disclosure by its ability to hybridize under stringent conditions to a nucleic acid otherwise determined to be within the scope of the disclosure (such as the exemplary sequences described herein).

The term "sequence identity" refers to a measure of similarity between amino acid or nucleotide sequences, and can be measured using methods known in the art, such as those described below. The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region, when compared and aligned for maximum correspondence over a comparison window, or designated region as measured using one of the following sequence comparison algorithms or by manual alignment and visual inspection.

The phrase "substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 25 bases or residues in length, about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below can be used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, Adv Appl Math, 2:482, 1981; by the homology alignment algorithm of Needleman and Wunsch, J Mol Biol, 48:443, 1970; by the search for similarity method of Pearson and Lipman, Proc Natl Acad Sci USA, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, Proc Natl Acad Sci USA, 85:2444, 1988; and Pearson, Methods Enzymol, 266:227-258, 1996). Preferred parameters used in a FASTA alignment of DNA sequences to calculate percent identity are optimized, BL50 Matrix 15:−5, k-tuple=2; joining penalty=40, optimization=28; gap penalty-12, gap length penalty=−2; and width=16.

Another preferred example of algorithms suitable for determining percent sequence identity and sequence similarity are the BLAST and BLAST 2.0 algorithms (Altschul et al., Nuc Acids Res, 25:3389-3402, 1977; and Altschul et al., J Mol Biol, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (Henikoff and Henikoff, Proc Natl Acad Sci USA, 89:10915, 1989) alignments (B) of 50, expectation (E) of 10, M=5, N=−4, and a comparison of both strands.

The BLAST algorithm also performs a statistical analysis of the similarity between two sequences (See, e.g., Karlin and Altschul, Proc Natl Acad Sci USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method (Feng and Doolittle, J Mol Evol, 35:351-360, 1987), employing a method similar to a published method (Higgins and Sharp, CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc Acids Res, 12:387-395, 1984).

Another preferred example of an algorithm that is suitable for multiple DNA and amino acid sequence alignments is the CLUSTALW program (Thompson et al., Nucl Acids. Res, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc Natl Acad Sci USA, 89:10915-10919, 1992).

The nucleic acid is "operably linked" when it is placed into a functional relationship with another nucleic acid sequence. For instance, a promoter or enhancer is operably linked to a coding sequence if it affects the transcription of the sequence.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

BRIEF DESCRIPTION

GBM is the most common and aggressive form of primary brain tumor and there is no curative treatment to date. Resistance to conventional therapies and tumor recurrence pose major challenges to treatment and management of this disease, and therefore new therapeutic strategies need to be developed. Previous studies by other investigators have shown that a subpopulation of GBM cells can grow as neurosphere-like cells when cultured in restrictive media, and exhibit enhanced tumor-initiating ability and resistance to therapy. As described herein, a large naive phage antibody display library was selected on the glycosylation-dependent CD133 epitope-positive subpopulation of GBM cells grown as tumor spheres. In this way, multiple human single chain antibodies (scFvs) that target GBM tumor sphere cells were identified. These scFvs were found to be efficiently internalized by GBM tumor sphere cells. One scFv GC4 inhibited self-renewal of GBM tumor sphere cells in vitro. A full-length human IgG1 based on this scFv was developed and found to potently inhibit proliferation of GBM tumor sphere cells and GBM cells grown in regular non-selective media.

DETAILED DESCRIPTION

The present disclosure is generally related to antibodies that bind specifically to glioblastoma multiforme (GBM) cells. In particular, the present disclosure provides compositions comprising human single chain or full-length antibodies that bind tumor cells. Additionally the present disclosure provides methods of using the anti-GBM antibodies.

Glioma tumor-initiating cells can be enriched by culturing primary tumor cells in serum free medium supplemented with epidermal growth factor (EGF) and basic fibroblast growth factor (bFGF) (Yuan et al., Oncogene, 23:9392-400, 2004). In this serum-free selective culture system, a subpopulation of GBM cells proliferates and forms tumor spheres. Moreover, these GBM tumor sphere cells more closely resemble the phenotype of primary tumors than do serum-cultured cell lines (Lee et al., Cancer Cell, 9:391-403, 2006), and demonstrate enhanced ability to self-renew and to give rise to differentiated progenies. As a result, these GBM tumor sphere cells provide an attractive target for the development of therapies targeting brain tumor-initiating cells.

Due to accessibility to externally administered agents, cell surface antigens are attractive targets for the development of therapeutics that require intracellular delivery of payloads (18, 19). Internalizing phage antibodies against a panel of tumor cell lines (20-25) and tumor cells in situ (26) were previously selected. Now GBM tumor spheres have been derived from human brain tumor specimens and the glycosylation-dependent CD133 epitope-positive subpopulation ("CD133 positive" population) have been targeted for phage antibody selection by FACS to recover internalizing scFvs. A panel of internalizing human scFvs that bind to CD133 positive GBM tumor sphere cells have been identified, and one of these scFvs is capable of inhibiting the growth of GBM tumor sphere cells in vitro. A full-length human IgG1 molecule based on this inhibitory scFv was developed and found to inhibit the proliferation of both GBM tumor sphere cells and primary GBM cells. These fully human antibodies and fragments thereof are suitable for diagnostic, prognostic and therapeutic applications, which target the subpopulation of tumor-initiating cells.

GBM tumor initiating cells have been well studied and are generally defined in two ways: by the expression of stem cell markers such as CD133 epitopes, and/or by the ability to grow in restrictive media (tumor sphere formation assay) (14, 15). Both methods have been widely used to enrich brain tumor initiating cells but each by itself may have limitations (16). Thus, in order to more precisely target GBM tumor initiating cells, GBM tumor sphere cells that express high levels of the CD133 epitope were used as the selection target. The use of two criteria to define prospective GBM tumor initiating cells used for antibody selection helps increase the chances of recovering antibodies targeting these cells.

The antibody library selection was performed on tumor sphere cells derived from fresh human GBM tissues and GBM tissues maintained in immunocompromised mice. Primary GBM tumors maintained as xenografts are useful for these studies for several reasons. First, these tumors have been well characterized, and shown to have the same gene alterations identified in their corresponding patient tumors (37). Secondly, a previous study has shown that brain tumors maintained as xenografts retain many features of the original tumors (27). Finally, these tumors can be propagated indefinitely, and thereby exist as a sustainable source of tissue for extended studies. Xenografts therefore provide a continuous supply of tissues with relatively consistent characteristics, and facilitate experimental reproducibility (27, 38).

The GBM tumor sphere cell-targeting scFvs disclosed herein can be used to develop monoclonal antibody-based therapeutics. For example, one of the disclosed scFvs (e.g., GC4) is able to inhibit self-renewal of GBM tumor sphere cells. Additionally, a full-length recombinant human GC4 IgG has been developed and, similar to the parental scFv, the GC4 IgG has been shown to inhibit proliferation of GBM tumor sphere cells. Moreover, even scFvs with no apparent anti-proliferation effects in vitro could nonetheless be useful for various clinical applications (e.g., diagnostic, prognostic, and/or therapeutic). Because the disclosed panel of scFvs has been selected for internalizing functions, they can be used as the basis for intracellular delivery strategies. For example, these internalizing scFvs can be conjugated to drugs or drug-loaded nanoparticles, engineered toxin molecules, or appropriate radionuclides to impart a targeted cell killing function (39, 40). Without wishing to be bound by theory, it is further believed that these targeted agents are suitable for in vivo ablation of tumor initiating cells, and suppression of subsequent recurrence.

Anti-GBM Antibodies

Certain aspects of the present disclosure relate to antibodies or fragments thereof that bind specifically to glioblastoma multiforme tumor cells. Preferably, the anti-GBM antibodies bind specifically to GBM tumor sphere cells, which in particularly preferred embodiments comprise GBM tumor-initiating cells. In certain embodiments, the anti-GBM antibodies inhibit the proliferation of GBM tumor cells. In other embodiments, the anti-GBM antibodies further inhibit self-renewal of GBM tumor cells Examples of anti-GBM antibodies that bind specifically to GBM tumor cells include, without limitation, the GC4 anti-GBM antibody, the GB1 anti-GBM antibody, the GB8 anti-GBM antibody, the GH9 anti-GBM antibody, and the GPD32 anti-GBM antibody.

In some embodiments, the anti-GBM antibody is the GC4 anti-GBM antibody, where the heavy chain variable regions, including the four framework regions, and the CDR1, CDR2, and CDR3 complementarity determining regions are set forth in SEQ ID NOs: 1-7; and the light chain variable regions, including the four framework regions, and the CDR1, CDR2, and CDR3 complementarity determining regions are set forth in SEQ ID NOs: 33-39. In some embodiments, the GC4 antibody is a variant GC4 antibody having a specified degree of amino acid sequence identity to the heavy chain variable region of SEQ ID NO: 8 and/or the light chain variable region of SEQ ID NO: 40, e.g., at least at least 90%, at least 91%, at least 92%, at least 93%, at least 94%, at least 95%, at least 96%, at least 97%, at least 98%, or even at least 99% sequence identity to SEQ ID NO: 8 and/or SEQ ID NO: 40.

In other embodiments, the GC4 anti-GBM antibody or fragment thereof comprises an antigen binding site that comprises a heavy chain comprising (i) complementarity determining region (CDR)-H1 of SEQ ID NO: 2, (ii) CDR-H2 of SEQ ID NO: 4, and (iii) CDR-H3 of SEQ ID NO: 6, and a light chain comprising (iv) CDR-L1 of SEQ ID NO: 34, (v) CDR-L2 of SEQ ID NO: 36, and (vi) CDR-L3 of SEQ ID NO: 38. In certain embodiments, the antigen binding site comprises a heavy chain variable region of SEQ ID NO: 8, and a light chain variable region of SEQ ID NO: 40.

In other embodiments, the anti-GBM antibody is the GB1 anti-GBM antibody, where the heavy chain variable regions, including the four framework regions, and the CDR1, CDR2, and CDR3 complementarity determining regions are set forth in SEQ ID NOs: 9-15; and the light chain variable regions, including the four framework regions, and the CDR1, CDR2, and CDR3 complementarity determining regions are set forth in SEQ ID NOs: 41-47. In some embodiments, the GB1 antibody is a variant GB1 antibody having a specified degree of amino acid sequence identity to the heavy chain variable region of SEQ ID NO: 16 and/or the light chain variable region of SEQ ID NO: 48, e.g., at least 90%, at least 91%, at least 92%, at least 93%, at least 94%, at least 95%, at least 96%, at least 97%, at least 98%, or even at least 99% sequence identity to SEQ ID NO: 16 and/or SEQ ID NO: 48.

In other embodiments, the GB1 antibody or fragment thereof comprises an antigen binding site that comprises a heavy chain comprising (i) complementarity determining region (CDR)-H1 of SEQ ID NO: 10, (ii) CDR-H2 of SEQ ID NO: 12, and (iii) CDR-H3 of SEQ ID NO: 14, and a light chain comprising (iv) CDR-L1 of SEQ ID NO: 42, (v) CDR-L2 of SEQ ID NO: 44, and (vi) CDR-L3 of SEQ ID NO: 46. In certain embodiments, the antigen binding site comprises a heavy chain variable region of SEQ ID NO: 16, and a light chain variable region of SEQ ID NO: 48.

In still other embodiments, the anti-GBM antibody is the GB8 antibody, where the heavy chain variable regions, including the four framework regions, and the CDR1, CDR2, and CDR3 complementarity determining regions are set forth in SEQ ID NOs: 17-23; and the light chain variable regions of GB8, including the four framework regions, and the CDR1, CDR2, and CDR3 complementarity determining regions are set forth in SEQ ID NOs: 49-55. In some embodiments, the GB8 antibody is a variant GB8 antibody having a specified degree of amino acid sequence identity to the heavy chain variable region of SEQ ID NO:24 and/or the light chain variable region of SEQ ID NO:56, e.g., at least 90%, at least 91%, at least 92%, at least 93%, at least 94%, at least 95%, at least 96%, at least 97%, at least 98%, or even at least 99% sequence identity to SEQ ID NO: 24 and/or SEQ ID NO: 56.

In yet other embodiments, the GB8 anti-GBM antibody or fragment thereof comprises an antigen binding site that comprises a heavy chain comprising (i) complementarity determining region (CDR)-H1 of SEQ ID NO: 18, (ii) CDR-H2 of SEQ ID NO: 20, and (iii) CDR-H3 of SEQ ID NO: 22, and a light chain comprising (iv) CDR-L1 of SEQ ID NO: 50, (v) CDR-L2 of SEQ ID NO: 52, and (vi) CDR-L3 of SEQ ID NO: 54. In certain embodiments, the antigen binding site comprises a heavy chain variable region of SEQ ID NO: 24, and a light chain variable region of SEQ ID NO: 56.

In further embodiments, the anti-GBM antibody is the GH9 anti-GBM antibody, where the heavy chain variable regions, including the four framework regions, and the CDR1, CDR2, and CDR3 complementarity determining regions are set forth in SEQ ID NOs: 25-31; and the light chain variable regions, including the four framework regions, and the CDR1, CDR2, and CDR3 complementarity determining regions are set forth in SEQ ID NOs: 57-63. In some embodiments, the GH9 antibody is a variant GH9 antibody having a specified degree of amino acid sequence identity to the heavy chain variable region of SEQ ID NO: 32 and/or the light chain variable region of SEQ ID NO:64, e.g., at least 90%, at least 91%, at least 92%, at least 93%, at least 94%, at least 95%, at least 96%, at least 97%, at least 98%, or even at least 99% sequence identity to SEQ ID NO: 32 and/or SEQ ID NO: 64.

In other embodiments, the GH9 anti-GBM antibody or fragment thereof comprises an antigen binding site that comprises a heavy chain comprising (i) complementarity determining region (CDR)-H1 of SEQ ID NO: 26, (ii) CDR-H2 of SEQ ID NO: 28, and (iii) CDR-H3 of SEQ ID NO: 30, and a light chain comprising (iv) CDR-L1 of SEQ ID NO: 58, (v) CDR-L2 of SEQ ID NO: 60, and (vi) CDR-L3 of SEQ ID NO: 62. In certain embodiments, the antigen binding site comprises a heavy chain variable region of SEQ ID NO: 32, and a light chain variable region of SEQ ID NO: 64.

In further embodiments, the anti-GBM antibody is the GPD32 anti-GBM antibody, where the heavy chain variable regions, including the four framework regions, and the CDR1, CDR2, and CDR3 complementarity determining regions are set forth in SEQ ID NOs: 66-72; and the light chain variable regions, including the four framework regions, and the CDR1, CDR2, and CDR3 complementarity determining regions are set forth in SEQ ID NOs: 74-80. In some embodiments, the GPD32 antibody is a variant GPD32 antibody having a specified degree of amino acid sequence identity to the heavy chain variable region of SEQ ID NO: 73 and/or the light chain variable region of SEQ ID NO: 81, e.g., at least 90%, at least 91%, at least 92%, at least 93%, at least 94%, at least 95%, at least 96%, at least 97%, at least 98%, or even at least 99% sequence identity to SEQ ID NO: 73 and/or SEQ ID NO: 81.

In other embodiments, the GPD32 anti-GBM antibody or fragment thereof comprises an antigen binding site that comprises a heavy chain comprising (i) complementarity determining region (CDR)-H1 of SEQ ID NO: 67, (ii) CDR-H2 of SEQ ID NO: 69, and (iii) CDR-H3 of SEQ ID NO: 71, and a light chain comprising (iv) CDR-L1 of SEQ ID NO: 75, (v) CDR-L2 of SEQ ID NO: 77, and (vi) CDR-L3 of SEQ ID NO: 79. In certain embodiments, the antigen binding site comprises a heavy chain variable region of SEQ ID NO: 73, and a light chain variable region of SEQ ID NO: 81.

In some embodiments, the anti-GBM antibodies of the present disclosure are fully human antibodies of any desired heavy chain isotype, including $IgA_1$, $IgA_2$, IgD, IgE, $IgG_1$, $IgG_2$, $IgG_3$, $IgG_4$, and IgM.

In other embodiments, the anti-GBM antibodies of the present disclosure are antibody fragments, including without limitation, Fab, $F(ab')_2$, Fv and Sfv fragments. Preferably the antibody fragments bind to and inhibit the proliferation of GBM tumor cells.

Other aspects of the present disclosure provide an isolated anti-GBM antibody or fragment thereof that competes for binding to glioblastoma multiforme (GBM) tumor sphere cells with any of the anti-GBM antibodies of the present disclosure.

The anti-GBM antibodies of the present disclosure may be recovered from a genetically engineered cell line, e.g. a Chinese Hamster Ovary (CHO) cell line expressing the anti-GBM antibody, or may be prepared by peptide synthesis.

Amino acid sequence modification(s) of the anti-GBM antibodies described herein are contemplated. For example, it may be desirable to improve the binding affinity and/or other biological properties of the antibodies. Amino acid sequence variants of an anti-GBM antibody are prepared by introducing appropriate nucleotide changes into the anti-GBM antibody nucleic acid, or by peptide synthesis. Such modifications include, for example, deletions from, and/or insertions into and/or substitutions of, residues within the amino acid sequences of the anti-GBM antibody. Any combination of deletion, insertion, and substitution is made to arrive at the final construct, provided that the final construct possesses the desired characteristics. The amino acid changes also may alter post-translational processes of the anti-GBM antibody, such as changing the number or position of glycosylation sites.

A useful method for identification of certain residues or regions of the anti-GBM antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the GBM antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-GBM antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-GBM antibody with an N-terminal methionyl residue or the antibody fused to a cytotoxic polypeptide. Other insertional variants of the anti-GBM antibody molecule include the fusion to the N- or C-terminus of the anti-GBM antibody to an enzyme (e.g. for ADEPT) or a polypeptide which increases the serum half-life of the antibody.

Another type of variant is an amino acid substitution variant. These variants have at least one amino acid residue in the anti-GBM antibody molecule replaced by a different residue. The sites of greatest interest for substitutional mutagenesis include the hypervariable regions or CDRs, but FR or Fc region alterations are also contemplated. Conservative substitutions are shown in Table 1 under the heading of "preferred substitutions". If such substitutions result in a change in biological activity, then more substantial changes, denominated "exemplary substitutions" in Table I, or as further described below in reference to amino acid classes, may be introduced and the products screened.

TABLE I

Amino Acid Substitutions

| Original Residue | Code | Acceptable Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, beta-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |

TABLE I-continued

Amino Acid Substitutions

| Original Residue | Code | Acceptable Substitutions |
|---|---|---|
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the anti-GBM antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and GBM tumor cells. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the anti-GBM antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, any oligosaccharide structure attached thereto may be altered. For example, antibodies with a mature carbohydrate structure that lacks fucose attached to an Fc region of the antibody are described in U.S. Pat Appl Nos. US 2003/0157108 and US 2004/0093621. Antibodies with a bisecting N-acetylglucosamine (GlcNAc) in the oligosaccharide structure attached to an Fc region of the antibody are referenced in WO03/011878, and U.S. Pat. No. 6,602,684. Antibodies with at least one galactose residue in an oligosaccharide structure attached to an Fc region of the antibody are reported in WO97/30087. See, also, WO98/58964 and WO99/22764 concerning antibodies with altered carbohydrate attached to the Fc region thereof. Antibody compositions comprising main species antibody with such carbohydrate structures attached to one or two heavy chains of the Fc region are contemplated herein.

Nucleic acid molecules encoding amino acid sequence variants of the anti-GBM antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-GBM antibody.

Immunoconjugates

The present disclosure also provides immunoconjugates comprising an anti-GBM antibody coupled to a functional moiety such as a detectable marker, a toxin (e.g. a small molecule toxin or an enzymatically active toxin of bacterial, fungal, plant or animal origin, including fragments and/or variants thereof), or a chemotherapeutic agent.

Non-limiting examples of detectable markers include a radioisotope (i.e., a radioconjugate), a metal chelator, an enzyme, a fluorescent compound, a bioluminescent compound, or a chemiluminescent compound.

Conjugates of an antibody and one or more small molecule toxins, such as a calicheamicin, a maytansine, a trichothene, and CC1065 are also contemplated herein. Toxins and fragments thereof which can be used include, without limitation, ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha sarcin, gelonin, mitogellin, retstrictocin, phenomycin, enomycin, curicin, crotin, calicheamicin, sapaonaria officinalis inhibitor, glucocorticoid, auristatin, auromycin, yttrium, bismuth, combrestatin, duocarmycins, dolostatin, cc 1065, and cisplatin.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1I and calicheamicin omega1I; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK®. polysaccharide complex (JHS Natural Products); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. The present disclosure further contemplates an immunoconjugate formed between an anti-GBM antibody and a compound with nucleolytic activity (e.g. a ribonuclease or a DNA endonuclease such as a deoxyribonuclease; DNase).

Conjugates of the anti-GBM antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described (Vitetta et al., Science, 238:1098, 1987).

Carbon-14-labeled 1-isothiocyanatobenzyl-3-methyldiethylene triaminepentaacetic acid (MX-DTPA) is an exemplary chelating agent for conjugation of radionucleotide to the antibody. The linker may be a "cleavable linker" facilitating release of the cytotoxic drug in the cell. For example, an acid-labile linker, peptidase-sensitive linker, dimethyl linker or disulfide-containing linker (Chari et al., Cancer Research, 52:127-131, 1992) may be used.

Alternatively, a fusion protein comprising an anti-GBM antibody and cytotoxic agent may be made, e.g. by recombinant techniques or peptide synthesis.

In yet another embodiment, the anti-GBM antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Additional Antibody Modifications

Other aspects of the present disclosure relate to other modifications of an anti-GBM antibody. For example, the anti-GBM antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

It may be desirable to modify the anti-GBM antibody of the present disclosure with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the anti-GBM antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an anti-GBM antibody can be engineered which has dual Fc regions and may thereby have enhanced complement lysis and ADCC capabilities. See Stevenson et al. Anti-Cancer Drug Design 3:219-230 (1989).

WO00/42072 describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642; U.S. Pat. No. 6,194,551; U.S. Pat. No. 6,242,195; U.S. Pat. No. 6,528,624; and U.S. Pat. No. 6,538,124. The antibodies comprise an amino acid substitution at one or more of amino acid positions 270, 322, 326, 327, 329, 313, 333 and/or 334 of the Fc region thereof.

To increase the serum half life of the anti-GBM antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG.sub.1, IgG.sub.2, IgG.sub.3, or IgG.sub.4) that is responsible for increasing the in vivo serum half-life of the IgG molecule. Antibodies with substitutions in an Fc region thereof and increased serum half-lives are also described in WO00/42072.

The anti-GBM antibodies disclosed herein may also be formulated as immunoliposomes. Liposomes containing the anti-GBM antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Recombinant Production of Antibodies

Anti-GBM antibodies of the present disclosure may also be produced in a host cell transfectoma using, for example, a combination of recombinant DNA techniques and gene transfection methods as is well known in the art (Morrison, Science, 229:1202, 1985). For instance to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s)

within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described (Goeddel, Gene Expression Technology, in Methods in Enzymology 185, Academic Press, San Diego, Calif., 1990). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter and polyoma. Alternatively, non-viral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., Mol Cell Biol, 8:466-472, 1988).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665; and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood, Immunology Today, 6:12-13, 1985).

Preferred mammalian host cells for expressing the recombinant antibodies of this disclosure include Chinese Hamster Ovary (CHO cells, including dhfr- CHO cells, Urlaub and Chasin, Proc Natl Acad Sci USA, 77:4216-4220, 1980; and Kaufman and Sharp, J Mol Biol, 159:601-621, 1982), NSO myeloma cells, COS cells and SP2 cells. In particular, for use with NSO myeloma cells, another preferred expression system is the GS gene expression system (See, e.g., Publication Nos. WO 87/04462; WO 89/01036 and EP 338,841). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Pharmaceutical Compositions

Other aspects of the present disclosure relate to compositions, e.g., pharmaceutical compositions, containing at least one anti-GBM antibody of the present disclosure or fragment thereof, formulated together with a pharmaceutically acceptable carrier. Such compositions may include, without limitation, one or a combination of (e.g., two or more different) antibodies, or immunoconjugates or bispecific antibodies of the present disclosure. As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

In some embodiments, therapeutic formulations of the disclosed antibodies are prepared for storage by mixing the antibody with optional pharmaceutically acceptable carriers, excipients, or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Additionally, the pharmaceutical compositions disclosed herein may contain more than one active compound as necessary for the particular indication being treated, preferably those with complementary activities that do not adversely affect each other. For example, it may be desirable to further provide antibodies which bind to EGFR or vascular endothelial factor (VEGF) in the one formulation. Alternatively, or additionally, the composition may further comprise a therapeutic agent, chemotherapeutic agent, toxin, cytotoxic agent, anti-tumor agent, cytokine, growth inhibitory agent, anti-hormonal agent, EGFR-targeted drug, anti-angiogenic agent, tyrosine kinase inhibitor, and/or cardioprotectant. Such molecules are suitably present in combination in amounts that are effective for the purpose intended.

Example of suitable anti-tumor agents include, without limitation, a chemotherapeutic, an angiogenesis inhibitor; a kinase inhibitor; a co-stimulation molecule blocker; an adhesion molecule blocker; an anti-cytokine antibody or functional fragment thereof; a corticosteroid; a non-steroidal anti-inflammatory agent, a nitrogen mustard, an aziridine, an alkyl sulfonate, a nitrosourea, a non-classical alkylating agent, a folate analog, a purine analog, an adenosine analog, a pyrimidine analog, a substituted urea, an antitumor antibiotic, an epipodophyllotoxin, a microtubule agent, a camptothecin analog, an enzyme, a cytokine, a monoclonal antibody, a recombinant toxin, an immunotoxin, a cancer gene therapy, a cancer vaccine, and a mixture thereof.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may also be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Pharmaceutical compositions to be used for in vivo administration must be sterile. This is readily accomplished by filtration through sterile filtration membranes.

Diagnostic and Prognostic Applications

Other aspects of the present disclosure relate to the use of the anti-GBM antibodies for diagnosing brain cancers, such as glioblastoma multiforme (GBM). Further aspects of the present disclosure relate to the use of anti-GBM antibodies for providing a prognosis of a brain cancer. For example, certain embodiments of the present disclosure relate to characterizing a biopsy sample for a patient by detecting the binding of the anti-GBM antibody to cells of the biopsy sample. In some embodiments, when the anti-GBM antibody binds to cells of the biopsy sample, the prognosis of the cancer patient is poor. Alternatively, when the anti-GBM antibody does not bind to cells of the biopsy sample, the prognosis of the cancer patient is good. In certain embodiments, detection of antibody binding is accomplished by contacting an anti-GBM antibody of the present disclosure with a biopsy sample from a patient having a brain tumor. In some embodiments, detection of binding of the anti-GBM antibody to cells of the biopsy sample is indicative that the biopsy sample is from a glioblastoma multiforme tumor.

Therapeutic Applications

Further aspects of the present disclosure relate to the therapeutic application of the anti-GBM antibodies. For example, certain embodiments of the present disclosure provide for the treatment of a brain tumor or small brain lesions, such as micrometastases, in a patient, by administering an effective amount of an anti-GBM antibody composition. Preferably, the brain tumor is a glioblastoma multiforme (GBM) tumor. In preferred embodiments, the anti-GBM antibody binds to GBM tumor-initiating cells. Without being bound by theory, it is believed that tumor-initiating cells are the primary force driving tumor recurrence, thus targeting these cells with the disclosed anti-GBM antibodies can result in improved treatment outcomes. Additionally, recent studies have shown that at least for some cancers, including GBM, tumor-initiating cells exist in a special vascular "niche" that renders them accessible to intravenously injected anti-GBM antibodies (e.g., Calabrese et al., Cancer Cell, 11:69-82, 2007; and Veeravagu et al., Stem Cells Dev, 17:859-67, 2008).

The brain tumor will generally be a GBM tumor containing GBM tumor-initiating cells. Accordingly, in certain embodiments, treatment with an anti-GBM antibody of the present disclosure results in the inhibition of the proliferation of GBM tumor-initiating cells. In other embodiments, the anti-GBM antibody further inhibits self-renewal of GBM tumor-initiating cells. Inhibition of cell proliferation and/or self-renewal may lead to improvement in the signs or symptoms of disease. For example, such therapy may result in an improvement in survival (overall survival and/or progression free survival) and/or may result in an objective clinical response (partial or complete). Preferably, the anti-GBM antibody is internalized by the GBM tumor cell, resulting in increased therapeutic efficacy of the anti-GBM antibody in killing the GBM tumor cell to which it binds.

In some embodiments, the anti-GBM antibody in the composition is a naked antibody. However, the anti-GBM antibody administered may also be coupled with a detectable marker, a toxin, or a chemotherapeutic agent. Non-limiting examples of detectable markers include radioisotopes, metal chelators, enzymes, fluorescent compounds, bioluminescent compounds, and chemiluminescent compounds. Non-limiting examples of suitable radioisotopes include $^{212}$Bi, $^{131}$I, $^{131}$In, $^{90}$Y, $^{186}$Re, $^{211}$At, $^{125}$I, $^{188}$Re, $^{153}$Sm, $^{213}$Bi, $^{32}$P, and $^{177}$Lu. Moreover, suitable toxins include, without limitation, ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha sarcin, gelonin, mitogellin, retstrictocin, phenomycin, enomycin, curicin, crotin, calicheamicin, sapaonaria officinalis inhibitor, glucocorticoid, auristatin, auromycin, yttrium, bismuth, combrestatin, duocarmycins, dolostatin, cc 1065, and cisplatin.

An anti-GBM antibody of the present disclosure is administered to a human patient in accordance with known methods, such as intravenous administration, e.g., as a bolus or by continuous infusion over a period of time. Alternatively, the anti-GBM antibody is administered intracranially.

For the treatment of brain tumors, an effective dosage of an anti-GBM antibody of the present disclosure will depend on the severity and course of the disease, previous therapy, the patient's clinical history and response to the anti-GBM antibody, and the discretion of the attending physician. The anti- GBM antibody is suitably administered to the patient at one time or over a series of treatments. Depending on the type and severity of the disease, about 1 μg/kg to 50 mg/kg (e.g. 0.1-20 mg/kg) of the anti-GBM antibody is an initial candidate dosage for administration to the patient, whether, for example, by one or more separate administrations, or by continuous infusion. In one embodiment, the initial infusion time for the anti-GBM antibody may be longer than subsequent infusion times, for instance approximately 90 minutes for the initial infusion, and approximately 30 minutes for subsequent infusions (if the initial infusion is well tolerated). The dosage of the anti-GBM antibody may be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the anti-GBM antibody). An initial higher loading dose, followed by one or more lower doses may be administered. In one embodiment, the anti-GBM antibody is administered as a loading dose of approximately 840 mg followed by approximately 420 mg approximately every 3 weeks. In another embodiment, the anti-GBM antibody is administered as a dose of approximately 1050 mg administered approximately every 3 weeks.

Other therapeutic agents may be combined with the anti-GBM antibody. Such combined administration includes coadministration or concurrent administration, using separate formulations or a single pharmaceutical formulation, and consecutive administration in either order, wherein preferably there is a time period while both (or all) active agents simultaneously exert their biological activities. Thus, the other therapeutic agent may be administered prior to, or following, administration of the anti-GBM antibody. In this embodiment, the timing between at least one administration of the other therapeutic agent and at least one administration of the anti-GBM antibody may be approximately 1 month or less, or approximately 2 weeks or less. Alternatively, the other therapeutic agent and the anti-GBM antibody are administered concurrently to the patient, in a single formulation or separate formulations.

Examples of other therapeutic agents that can be combined with the anti-GBM antibody include, without limitation any one or more of: a chemotherapeutic agent, an angiogenesis inhibitor; a kinase inhibitor; a co-stimulation molecule blocker; an adhesion molecule blocker; an anti-cytokine antibody or functional fragment thereof; a corticosteroid; a non-steroidal anti-inflammatory agent, a nitrogen mustard, an aziridine, an alkyl sulfonate, a nitrosourea, a non-classical alkylating agent, a folate analog, a purine analog, an adenosine analog, a pyrimidine analog, a substituted urea, an anti-tumor antibiotic, an epipodophyllotoxin, a microtubule agent, a camptothecin analog, an enzyme, a cytokine, a monoclonal antibody, a recombinant toxin, an immunotoxin, a cancer gene therapy, and a cancer vaccine.

Suitable dosages for any of the above coadministered agents are those presently used and may be lowered due to the combined action (synergy) of the agent and anti-GBM antibody. Treatment with the combination of the anti-GBM antibody composition and other therapeutic agent may result in a synergistic, or greater than additive, therapeutic benefit to the patient.

If a chemotherapeutic agent is administered, it is usually administered at dosages known therefor, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In addition to the above therapeutic regimes, the patient may be subjected to radiation therapy and/or surgical resection of the tumor cells.

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: ° C. (degrees Centigrade); $H_2O$ (water); by (base pair); kb (kilobase pair); kD (kilodaltons); gm (grams); μg and ug (micrograms); mg (milligrams); ng (nanograms); μl and ul (microliters); ml (milliliters); cm (centimeters); mm (millimeters); nm (nanometers); μm and um (micrometer); M (molar); mM (millimolar); μM and uM (micromolar); nM (nanomolar); MW (molecular weight); h (hour); min (minute); mAb (monoclonal antibody); IgG (immunoglobulin); DMEM (Dulbecco's modified Eagle's medium); TSFM (tumor sphere forming media); FCS (fetal calf serum); BSA (bovine serum albumin); bFGF (basic fibroblast growth factor); PBS (phosphate buffered saline); EGF (epidermal growth factor); PE (phycoerythrin); FITC (fluorescein isothiocyanate); FACS (fluorescence-activated cell sorting); NaCl (sodium chloride); DAPI (4',6-diamidino-2-phenylindole); Q-dot (quantum dot); scFv (single-chain variable fragment); and GBM (glioblastoma multiforme).

Example 1

Identification of Antibodies Targeting Brain Tumor Sphere Cells

The following example describes the development of GBM tumor spheres from human brain tumor specimens, and the results of a phage antibody selection for internalizing scFvs by targeting the glycosylation-dependent CD133 epitope-positive subpopulation (hereinafter referred to as "CD133 positive"). Additionally, the following example describes the identification of internalizing human scFvs that bind to CD133 positive GBM tumor sphere cells, and that inhibit the growth of GBM tumor sphere cells in vitro. This example also describes a full-length human IgG1 molecule derived from an inhibitory scFv that inhibits the proliferation of both GBM tumor sphere cells and primary GBM cells.

Materials and Methods

Culture of Primary Glioblastoma Cells and Tumor Sphere Cells:

Human GBM tissues obtained from the operating room were either processed immediately or transplanted and maintained in nude mice as xenografts as described (27). The protocol for human tissue acquisitions was approved by the Institutional Review Board and in accordance with an assurance filed with and approved by the Department of Health and Human Services. Animal studies were approved by the Institutional Review Board and adhered to the U.S. Public Health Service Policy on Humane Care and Use of Laboratory Animals. The procedure for obtaining tumor sphere cell cultures is the same for fresh GBM tissues or GBM xenografts. Briefly, GBM tissues were minced, and enzymatically dissociated by sequential digestion with collagenase (1 mg/ml, Invitrogen) and trypsin (0.05%, Invitrogen), and passed through a cell strainer (BD Biosciences) to obtain monodispersed cells. These cells were divided into two groups and were either (1) resuspended in DMEM/F12 containing 2% fetal calf serum (FCS) and then plated at a density of $1 \times 10^6$ cells per 75 $cm^2$ flask to obtain primary GBM cell monolayer cultures, or (2) seeded into tumor sphere forming media (TSFM) containing serum-free Complete NeuroCult medium (StemCell Technologies) supplemented with 10 ng/ml bFGF (Millipore/Chemicon), 10 ng/ml EGF (Sigma) and 0.2% heparin/PBS (StemCell Technologies). For serial propagation, primary tumor spheres were re-dissociated into monodispersed cells by trypsin digestion and further cultured in TSFM.

Cloning Efficiency Assay:

The tumor spheres were treated with 0.05% trypsin and passed through a cell strainer to obtain monodispersed cells and plated into a 96-well plate (1,000 cells/well) and cultured in 200 µl TSFM for 14 days (28). Cells were fed with 25 µl of TSFM by changing medium every 2 days. Experiments were done in triplicates. The number of tumor spheres were counted and averaged to determine the cloning efficiency (15, 29).

Flow Cytometry Analysis of CD133 Epitope Expression:

Primary GBM cells and tumor sphere cells were dissociated by 0.05% trypsin, washed with PBS, and 100 µl aliquots of $10^5$ cells in PBS were placed in 96-well V-bottom plates and incubated on ice for 30 min with phycoerythrin (PE)-conjugated anti-CD133 antibody (Miltenyi Biotec) or an isotype control PE-labeled mouse IgG (BD/Pharmingen). Cells were washed twice with PBS and analyzed by FACS (LSRII, Becton Dickinson).

Selection for Internalizing scFvs Targeting GBM Tumor Sphere Cells:

A multivalent fd phage antibody display library containing the Sheets repertoire (30, 31) was used for selection on GBM tumor sphere cells that express high levels of the CD133 epitope. For the first round of selection, the library was counter-selected on a panel of control cells to remove non-specific binders as described (22, 24, 26), and incubated for 2 h at 4° C. with $10^5$ monodispersed GBM sphere cells, washed three times with ice-cold PBS, then incubated with pre-warmed (37° C.) DMEM/F12 containing 10% FCS at 37° C. for 1 h to allow receptor-mediated phage antibody internalization (22, 24). Non-internalized phage were removed by washing cells with 50 mM glycine/150 mM NaCl, pH 2.8. Internalized phage were recovered and propagated as described previously (22, 24, 26). For the second round of selection, tumor sphere cells were incubated with polyclonal round one phage under internalizing conditions as described above and further incubated with the PE-conjugated anti-CD133 antibody to identify subpopulations expressing high levels of CD133, which were sorted by FACSAria (Becton Dickinson) along with internalized phage. The process was repeated for the third round of selection. Monoclonal phage binders were identified by FACS-based 96-well plate screening using biotin-labeled anti-fd antibody (Sigma) and streptavidin-R-PE (Invitrogen) as described (22, 24, 26).

Double-Labeling of the CD133 Epitope and Antigens Bound by Phage Antibodies:

Phage antibodies were fluorescently labeled using 6-(fluorescein-5-[and -6]-carboxamido)hexanoic acid, succinimidyl ester (5(6)-SFX) (Invitrogen) and purified as described (22, 32, 33). Monodispersed GBM sphere cells were incubated with biotin-labeled anti-CD133 mAb (5 µg/ml, Miltenyi Biotec) and FITC-labeled phage antibodies. Streptavidin-647 (Invitrogen) was used to detect bound biotin-labeled anti-CD133 antibody.

Phage Antibody Binding to Antigens Other than CD133:

Caco-2 cells that express high levels of CD133 were incubated with phage antibodies along with the positive control PE-conjugated anti-CD133 antibody at 4° C. for 1 h, washed twice with PBS, and bound phage detected by biotin-labeled anti-fd antibody followed by streptavidin-R-PE, and analyzed by FACS. For immunoprecipitation studies, $10^5$ Caco-2 cells were lysed in 1% NP40, 0.15 M NaCl, and 0.01 M sodium phosphate, pH 7.2, on ice for 2 h. Lysates were pre-cleared and incubated with 50 µg/ml scFvs bearing a hexahistidine tag at 4° C. for 1 h, and captured onto Ni-NTA+ beads (Qiagen). As a positive control, precleared Caco-2 lysates were incubated with rabbit anti-CD133 antibody (Cell Signaling Technology) followed by capturing with protein A beads (Thermo Fisher Scientific). All immunoprecipitation products were analyzed by 4-20% gradient SDS-PAGE, followed by Western blot with mouse anti-CD133 followed by horseradish peroxidase-conjugated goat anti-mouse antibody (Jackson ImmunoResearch) using ECL Plus™ (GE Healthcare).

Expression and Purification of Recombinant scFvs:

ScFvs were subcloned from the phage vector into a bacteria expression vector, resulting in the addition of a c-myc epitope and a hexahistidine tag at the C-terminus as described (22). ScFv was harvested from the bacterial periplasm (22) and purified using AKTAprime (GE HealthCare) by immobilized metal affinity chromatography (HiTrap His, GE HealthCare) and gel filtration (PD10, GE HealthCare), and analyzed by reducing 10% SDS-PAGE (22, 23).

ScFv Internalization by Tumor Sphere Cells:

ScFvs were labeled with Q-dot (655) using a two-step conjugation procedure as described (25), incubated with tumor sphere cells at 37° C. for 1 hr, washed with PBS and fixed in 2% paraformaldehyde (Sigma), and viewed under a fluorescence microscope (Olympus) and a confocal microscope (Zeiss). DAPI (nucleus) and Q-dot labeled phage antibodies were imaged in separate channels and merged to show scFv subcellular location. To broaden applicability, we labeled scFvs with FITC using 5(6)-SFX and repeated the binding and internalization experiments. Quantification of internalized phage antibodies was performed as described (22). Briefly, $1 \times 10^5$ GBM sphere cells were incubated with phage antibodies at 37° C. for 1 h and 4 h respectively, washed with PBS, and divided evenly into two groups, one for quantification of the total phage bound, and the other for the internalized fraction following surface stripping with 50 mM glycine/150 mM NaCl, pH 2.8.

Inhibition of Self-Renewal of GBM Tumor Sphere Cells by Recombinant scFvs:

One thousand monodispersed tumor sphere cells were incubated with GC4 scFv (50 µg/ml) in 200 µl TSFM. Media were changed every 2 days by replacing 25 µl of old media with fresh media containing 50 µg/ml scFvs. Colonies (tumor spheroids) were counted after 14 days.

Generation of a Recombinant Human GC4 IgG1 Molecule:

The sequence information of the GC4 scFv was used to develop the human IgG1 as described previously (34). Briefly, the GC4 VH was amplified using primer pairs with overhangs containing MluI and NheI sites, digested with MluI and NheI, ligated into a mammalian expression vector to create in frame fusion with the human heavy chain constant region. The VL gene was amplified with the primer pairs with overhangs containing DraIII and AvrII, and ligated into DraIII- and KpnI-digested plasmid containing the GC4 heavy chain gene to create a plasmid that expresses both heavy and light chains, which was used to transfect CHO-DG44 cells by electroporation and to establish stable lines by selecting with G418 as described previously (34, 35). GC4 IgG1 was purified on a protein A column using the AKTA protein purification system (GE Healthcare), and analyzed by SDS-PAGE under reducing conditions. IgG concentration was measured using Nanodrop (Thermal Fisher Scientific).

Affinity Measurement:

Varying concentrations of GC4 IgG1s were incubated with $10^5$ GBM cells at RT for 1 h in PBS containing 0.25% BSA. Bound IgG1s were detected by PE-conjugated goat anti-human antibody (Jackson ImmunoResearch) following incubation at RT for 30 min. Apparent dissociation constant was determined by FACS with mean fluorescence intensity (MFI) data fitted using GraphPad Prism (GraphPad Software). The apparent dissociation constant of GC4 scFv was measured similarly except that bound scFvs were detected by mouse anti-hexahistidine antibody (AbD Serotec/MorphoSys) followed by PE-conjugated goat anti-mouse antibody (Jackson ImmunoResearch).

Inhibition of GMB Cell Proliferation by Human GC4 IgG1:

To test the effect of GC4 IgG1 on tumor sphere cells, 1,000 monodispersed tumor sphere cells were incubated with 50 μg/ml GC4 IgG1 in 200 μl TSFM, and placed in a 96-well plate. There were no significant aggregations of tumor sphere cells under this condition. Media were changed every 2 days by replacing 25 μl of old media with fresh media containing 50 μg/ml GC4 IgG1. Tumor spheres were counted after 14 days. The assay was done in parallel with a control non-binding human IgG1 (34). To test the effect of GC4 IgG1 on GBM cells grown in non-selective media, soft agar assays were performed. Briefly, 300 μl melted 0.5% agarose was added to a 24-well plate and allowed to solidify. To prepare the top layer, 2.5% SeaPlaque low-melting temperature agarose (Cambrex Bioscience) was melted and diluted (v/v 1:7, final 0.35%) in RPMI-1640/10% FCS media, and kept at 42° C. in a water bath. Ten thousand monodispersed GBM cells were mixed with human IgG1s (at a final concentration of 50 μg/ml) in 300 μl 0.35% low-melting temperature agarose. The mixture was applied to the top of the solidified agarose in the 24-well plate and kept at RT for 30 min to allow solidification of the top layer. The plate was then incubated at 37° C. and colonies were counted after 14 days (36).

Growth Inhibition of Established Tumor Spheres:

Monodispersed tumor sphere cells were placed in 6-well plates in TSFM at a density of 200 cells per well and allowed to grow for 2-3 days to form tumor spheroids. The GC4 scFv was added to a final concentration of 50 μg/ml and the incubation continued for an additional 4-5 days. The number of tumor spheres with a diameter greater than 50 μm was counted under an inverted microscopy (Nikon).

Statistics:

The Student's t test was used to analyze a pair of variables, and a P value of <0.05 was considered statistically significant.

Results

Isolation and Characterization of GBM Tumor Sphere Cells.

Figure 1B:
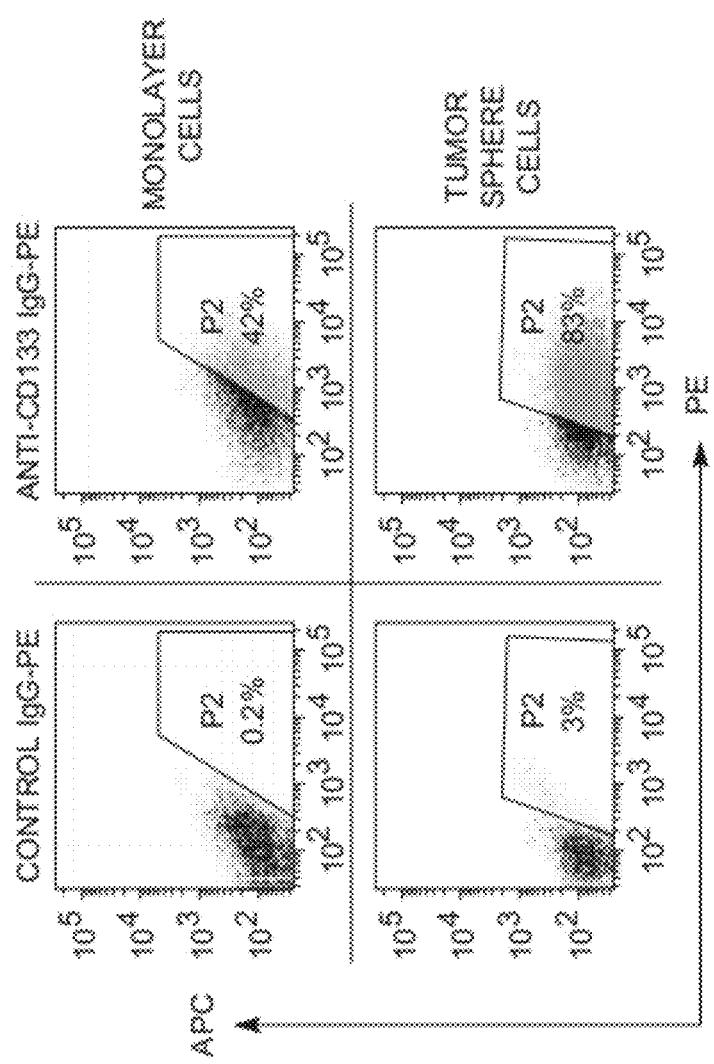
FIG. 1B depicts CD133 epitope expression by GBM cells grown as a monolayer in serum containing media or as tumor spheres in serum free media.

GBM tumor spheres were isolated from five fresh human surgical specimens, as well as from nine human GBM tissues maintained as xenografts in immunocompromised mice, by growing dissociated GBM cells in restrictive media containing bFGF and EGF. Tumor spheres consisting of a few hundred to a few thousand cells became visible after 7-14 days of culture (FIG. 1). The cloning efficiency of tumor spheres grown in restrictive media was then compared to that of bulk tumor cells from fresh surgical GBM specimens and GBM xenografts grown in media containing serum. GBM tumor sphere cells have higher cloning (self-renewal) capacity than either of the bulk tumor cells (about 10-20% vs. 1-2%), consistent with reports by others (15). The expression of the CD133 epitope (AC141) was then analyzed on GBM tumor sphere cells and GBM cells grown as monolayer cultures in non-selective media containing 2% FCS. Levels of CD133 epitope expression were detectable in 11 out of 14 GBM cultures (grown as spheres or monolayer cells) (FIG. 1 and Table 1-1). In most cases (10/11) where epitope expression was evident, tumor sphere cells expressed higher levels of the CD133 epitope than the equivalent cells cultured as a monolayer in non-selective media. In addition, the expression of the CD133 epitope usually remained stable for a longer period of time in tumor sphere cells compared to monolayer primary tumor (4-6 months compared to about 1-2 months).

TABLE 1-1

Tumor Sphere Formation and CD133 Epitope Expression

| GBM Tissues | Tumor sphere formation | CD133 epitope expression | Target tissues for initial selection | Tissues used for re-test |
|---|---|---|---|---|
| GBMx-1 | ++ | 80% | | + |
| GBMx-2 | ++ | 50% | | + |
| GBMx-3 | ++ | 2% | | + |
| GBMx-4 | ++ | 0* | | + |
| GBMx-5 | ++ | 3% | | + |
| GBMx-6 | ++ | 4% | | + |
| GBMx-7 | ++ | 15% | | + |
| GBMx-8 | ++ | 70% | + | + |
| GBMx-9 | ++ | 0* | | |
| GBMh-1 | + | 0* | | |
| GBMh-2 | ++ | 12% | + | + |
| GBMh-3 | + | 8% | | |
| GBMh-4 | ++ | 3% | | + |
| GBMh-5 | + | 6% | | |

For Table 1-1, "GBMh" indicates human GBM tissues, "GBMx" indicates GBM maintained as xenografts in nude mice, "++" indicates large size spheres containing >100 cells per sphere after 14 days of incubation, "+" indicates small size spheres containing <100 cells per sphere after 14 days of incubation, and "0*" indicates expression levels that are indistinguishable from that of the control (control isotype-matched mouse IgG stain). GBMx-8 and GBMh-2 were used for initial phage antibody library selection. Positive binders were re-tested on additional GBM tissues as indicated.

Selection of Internalizing Human scFvs Targeting the CD133 Positive Subpopulation of Tumor Sphere Cells.

Figure 2A:
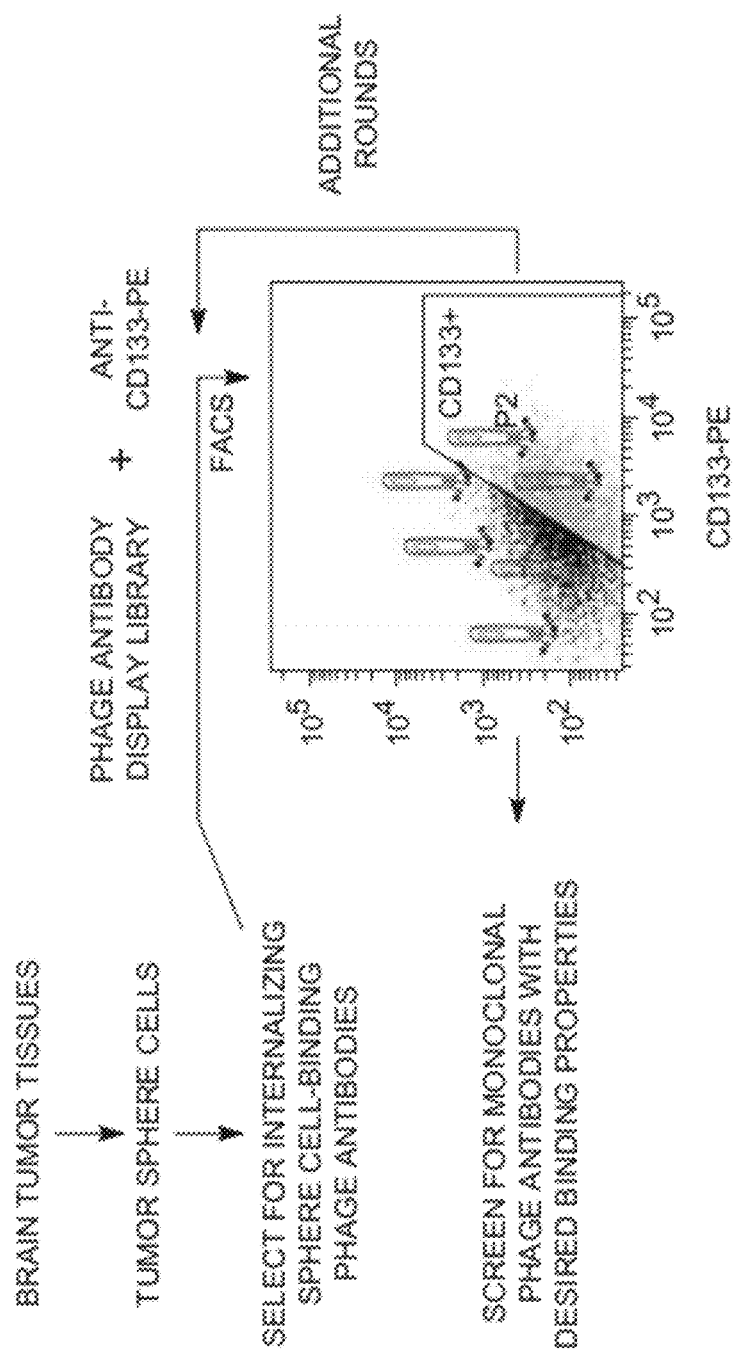
FIG. 2A depicts an outline of the selection scheme. Selection was performed by FACS on cells derived from multiple GBM cases. CD133+ cells were gated by comparing to staining results with an isotype-matched PE-conjugated control mouse mAb. Outputs from round-3 selections were screened to identify monoclonal phage antibodies.

For phage antibody library selection (FIG. 2A), CD133 positive tumor sphere cells derived from fresh human GBM tissues (GBMh2) were initially targeted to increase the likelihood of identifying scFvs that target clinically represented markers. For subsequent rounds of selection the CD133 positive fraction of tumor sphere cells derived from GBM tissues maintained as xenografts (GBMx-8) were targeted. To broaden applicability, positive binders were re-tested on additional GBM tissues (Table 1-4).

Figure 2B:
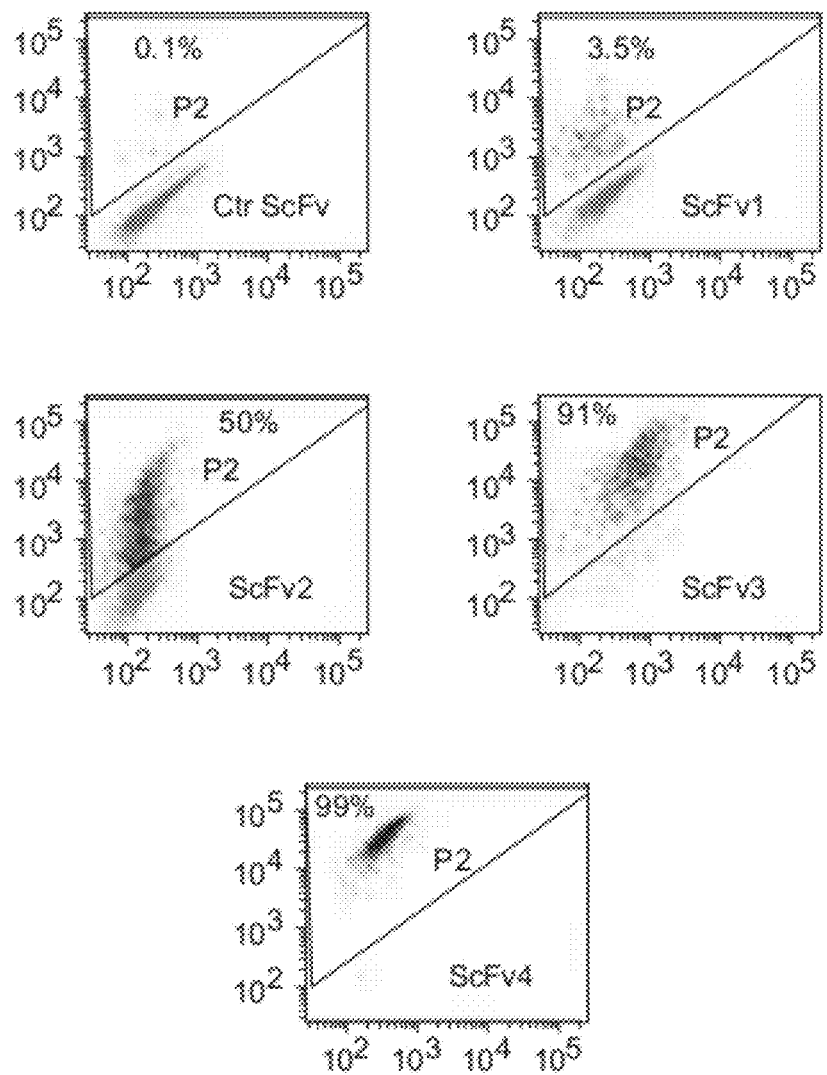
FIG. 2B depicts patterns of phage antibody binding to GBM cells. Percentage of positive cells is indicated. GBMx8 tumor sphere cells were used in the analysis.

To begin, the 500 million-member naïve phage antibody display library was counter-selected on a panel of non-tumorigenic cell lines to remove non-specific binders, and then the library was selected on GBM tumor sphere cells under internalizing conditions to enrich polyclonal phage that target internalizing epitopes. The polyclonal phage antibodies were then used as the input for further selection by FACS to target the CD133 positive cells. After two rounds of FACS-based selection, the selection output for binding to GBM sphere cells was analyzed. About 45% (83/186) of phage antibodies bound to GBM sphere cells but not control cells such as BPH-1. There were twenty unique scFvs among sixty that were sequenced. The phage antibodies exhibit a range of binding patterns, binding from about 3% to 99% of the GBM sphere cell population (FIG. 2B). Five scFvs with the highest frequency of representations in the output were chosen for further studies (Table 1-4). These five scFVs were re-tested and validated on additional GBM tissues not used in the initial selection (Table 1-4). By scanning a sequence database of previously identified scFvs, one scFv that binds to all GBM sphere cells was found to be identical to H3, an scFv that had previously been identified and shown to bind to an internalizing epitope on ALCAM/CD166 (26, 34). To simplify the nomenclature, the original name H3 was used to designate this scFv. The other four scFvs, GC4, GB1, GB8, and GH9, have not been previously identified. In addition, a second ALCAM/CD166 binding scFv, GPD32, with a new sequence has been identified.

The heavy chain variable regions of GC4, including the four framework regions, and the CDR1, CDR2, and CDR3 complementarity determining regions are set forth in SEQ ID NOs: 1-7, respectively. The light chain variable regions of GC4, including the four framework regions, and the CDR1, CDR2, and CDR3 complementarity determining regions are set forth in SEQ ID NOs: 33-39, respectively. The antigen binding site of GC4 comprises a heavy chain variable region of SEQ ID NO: 8, and a light chain variable region of SEQ ID NO: 40.

The heavy chain variable regions of GB1, including the four framework regions, and the CDR1, CDR2, and CDR3 complementarity determining regions are set forth in SEQ ID NOs: 9-15, respectively. The light chain variable regions of GB1, including the four framework regions, and the CDR1, CDR2, and CDR3 complementarity determining regions are set forth in SEQ ID NOs: 41-47, respectively. The antigen binding site of GB1 comprises a heavy chain variable region of SEQ ID NO: 16, and a light chain variable region of SEQ ID NO: 48.

The heavy chain variable regions of GB8, including the four framework regions, and the CDR1, CDR2, and CDR3 complementarity determining regions are set forth in SEQ ID NOs: 17-23, respectively. The light chain variable regions of GB1, including the four framework regions, and the CDR1, CDR2, and CDR3 complementarity determining regions are set forth in SEQ ID NOs: 49-55, respectively. The antigen binding site of GB8 comprises a heavy chain variable region of SEQ ID NO: 24, and a light chain variable region of SEQ ID NO: 56.

The heavy chain variable regions of GH9, including the four framework regions, and the CDR1, CDR2, and CDR3 complementarity determining regions are set forth in SEQ ID NOs: 25-31, respectively. The light chain variable regions of GB1, including the four framework regions, and the CDR1, CDR2, and CDR3 complementarity determining regions are set forth in SEQ ID NOs: 57-63, respectively. The antigen binding site of GB1 comprises a heavy chain variable region of SEQ ID NO: 32, and a light chain variable region of SEQ ID NO: 64. The heavy chain variable regions of GPD32, including the four framework regions, and the CDR1, CDR2, and CDR3 complementarity determining regions are set forth in SEQ ID NOs: 66-72, respectively. The light chain variable regions of GPD32, including the four framework regions, and the CDR1, CDR2, and CDR3 complementarity determining regions are set forth in SEQ ID NOs: 74-80, respectively. The antigen binding site of GPD32 comprises a heavy chain variable region of SEQ ID NO: 73, and a light chain variable region of SEQ ID NO: 81.

TABLE 1-2

Heavy Chain Variable Region Sequences

| Clone | Region | Heavy Chain Sequence | SEQ ID |
|---|---|---|---|
| GC4 | Frame 1 | QVQLVESGGGLVQPGGSLRLSC AASGFTFG | NO: 1 |
| | CDR1 | TYDMS | NO: 2 |
| | Frame 2 | WVRQAPGKGLEWVS | NO: 3 |
| | CDR2 | GISGSGGSTYYADSVKG | NO: 4 |
| | Frame 3 | RFTISRDNSKNTVYLQMNSLRV EDTAVYYCAR | NO: 5 |
| | CDR3 | GGWYSDN | NO: 6 |
| | Frame 4 | WGQGTLVTVSS | NO: 7 |
| | Variable (Frame 1 to 4) | QVQLVESGGG LVQPGGSLRL SCAASGFTFG TYDMSWVRQA PGKGLEWVSG ISGSGGSTYY ADSVKGRFTI SRDNSKNTVY LQMNSLRVED TAVYYCARGG WYSDNWGQGT LVTVSS | NO: 8 |
| GB1 | Frame 1 | QVQLVQSGGGLVKPGGSLRLS CAASGFTFS | NO: 9 |
| | CDR1 | NAWMN | NO: 10 |
| | Frame 2 | WVRQAPGKGLEWVG | NO: 11 |
| | CDR2 | RIKSKTDGGTTDYAAPVNG | NO: 12 |
| | Frame 3 | RFTISRDDSKNTLYLQMNSLK TEDTAVYSCTT | NO: 13 |
| | CDR3 | ENWGSVN | NO: 14 |
| | Frame 4 | WGQGTLVTVSS | NO: 15 |
| | Variable (Frame 1 to 4) | QVQLVQSGGG LVKPGGSLRL SCAASGFTFS NAWMNWVRQA PGKGLEWVGR IKSKTDGGTT DYAAPVNGRF TISRDDSKNT LYLQMNSLKT EDTAVYSCTT ENWGSVNWGQ GTLVTVSS | NO: 16 |
| GB8 | Frame 1 | QVQLVESGGGLVQPGGSLRLS CAASGFTFS | NO: 17 |
| | CDR1 | NYALT | NO: 18 |
| | Frame 2 | WVRQAPGKGLEWVS | NO: 19 |
| | CDR2 | AISGSGGSTYYADSVKG | NO: 20 |
| | Frame 3 | RFTISRDTSKNTLYLQMNSLR AEDTAVYYCAR | NO: 21 |
| | CDR3 | GGYSYGPPFDY | NO: 22 |
| | Frame 4 | WGQGTLVTVSS | NO: 23 |
| | Variable (Frame 1 to 4) | QVQLVESGGG LVQPGGSLRL SCAASGFTFS NYALTWVRQA PGKGLEWVSA ISGSGGSTYY ADSVKGRFTI SRDTSKNTLY LQMNSLRAED TAVYYCARGG YSYGPPFDYW GQGTLVTVSS | NO: 24 |
| GH9 | Frame 1 | QVQLQESGGGLVKPGGSLRLS CAASGFTFS | NO: 25 |
| | CDR1 | SYSMN | NO: 26 |
| | Frame 2 | WVRQAPGQGLEWVS | NO: 27 |
| | CDR2 | SISSRNSDIYYADSVRG | NO: 28 |
| | Frame 3 | RFTISRDNAKNSLYLQMNSLR AEDTAVYYCAR | NO: 29 |
| | CDR3 | DSSGYSSSPSDY | NO: 30 |
| | Frame 4 | WGQGTLVTVSS | NO: 31 |
| | Variable (Frame 1 to 4) | QVQLQESGGG LVKPGGSLRL SCAASGFTFS SYSMNWVRQA PGQGLEWVSS ISSRNSDIYY ADSVRGRFTI SRDNAKNSLY LQMNSLRAED TAVYYCARDS SGYSSSPSDY WGQGTLVTVS S | NO: 32 |

TABLE 1-2-continued

Heavy Chain Variable Region Sequences

| Clone | Region | Heavy Chain Sequence | SEQ ID |
|---|---|---|---|
| GPD32 | Frame 1 | QVQLQESGGGLVQPGGSLRLS CAASGFTFS | 66 |
|  | CDR1 | SYALS | 67 |
|  | Frame 2 | WVRQAPGKGLEWVS | 68 |
|  | CDR2 | AISGSGGSTYYAGSVKG | 69 |
|  | Frame 3 | RFTISRDNSKNTLYLQMNSLR AEDTAVYYCAK | 70 |
|  | CDR3 | GLIASH | 71 |
|  | Frame 4 | WGQGTLVTVSS | 72 |
|  | Variable (Frames 1 to 4) | QVQLQESGGG LVQPGGSLRL SCAASGFTFS SYALSWVRQA PGKGLEWVSA ISGSGGSTYY AGSVKGRFTI SRDNSKNTLY LQMNSLRAED TAVYYCAKGL IASHWGQGTL VTVSS | 73 |

TABLE 1-3

Light Chain Variable Region Sequences

| Clone | Region | Light Chain Sequence | SEQ ID |
|---|---|---|---|
| GC4 | Frame 1 | SELTQDPAVSVALGQTVRITC | NO: 33 |
|  | CDR1 | QGGSLRSYYAS | NO: 34 |
|  | Frame 2 | WYQQKPGQAPLLVI | NO: 35 |
|  | CDR2 | YGENNRPS | NO: 36 |
|  | Frame 3 | GIPDRFSGSSSGNTASLTI TGAQAEDEADYYC | NO: 37 |
|  | CDR3 | HSRDSSGNHVV | NO: 38 |
|  | Frame 4 | FGGGTKLTV | NO: 39 |
|  | Variable (Frame 1 to 4) | SELTQDPAVS VALGQTVRIT CQGGSLRSYY ASWYQQKPGQ APLLVIYGEN NRPSGIPDRF SGSSSGNTAS LTITGAQAED EADYYCHSRD SSGNHVVFGG GTKLTV | NO: 40 |
| GB1 | Frame 1 | NFMLTQPPSVSVAPGKTASLTC | NO: 41 |
|  | CDR1 | GYNIGTKSVH | NO: 42 |
|  | Frame 2 | WYQQKPGQAPVVVV | NO: 43 |
|  | CDR2 | HDDSDRPS | NO: 44 |
|  | Frame 3 | GIPERFSGSNSGTTATLTI SRVEAGDEADYYC | NO: 45 |
|  | CDR3 | QAWDSISEEVV | NO: 46 |
|  | Frame 4 | FGGGTKLTV | NO: 47 |
|  | Variable (Frames 1 to 4) | NFMLTQPPSV SVAPGKTASL TCGYNIGTKS VHWYQQKPGQ APVVVVHDDS DRPSGIPERF SGSNSGTTAT LTISRVEAGD EADYYCQAWD SISEEVVFGG GTKLTV | NO: 48 |
| GB8 | Frame 1 | SELTQDPAVSVALGQTVRITC | NO: 49 |
|  | CDR1 | QGDSLRSYYAS | NO: 50 |

TABLE 1-3-continued

Light Chain Variable Region Sequences

| Clone | Region | Light Chain Sequence | SEQ ID |
|---|---|---|---|
|  | Frame 2 | WYQQKPGQAPVLVI | NO: 51 |
|  | CDR2 | YGKNKRPS | NO: 52 |
|  | Frame 3 | GIPDRFSGSSSGNTASLTI TGAQAVDEADYHC | NO: 53 |
|  | CDR3 | NSRDSSGNHVV | NO: 54 |
|  | Frame 4 | FGGGTKLTV | NO: 55 |
|  | Variable (Frames 1 to 4) | SELTQDPAVS VALGQTVRIT CQGDSLRSYY ASWYQQKPGQ APVLVIYGKN KRPSGIPDRF SGSSSGNTAS LTITGAQAVD EADYHCNSRD SSGNHVVFGG GTKLTV | NO: 56 |
| GH9 | Frame 1 | NFMLTQPPSVSVAPGKTASLTC | NO: 57 |
|  | CDR1 | GGYNIGTKSVH | NO: 58 |
|  | Frame 2 | WYQQKPGQAPVVVV | NO: 59 |
|  | CDR2 | HDDSDRPS | NO: 60 |
|  | Frame 3 | GIPERFSGSNSGTTATLTI SRVEAGDEADYYC | NO: 61 |
|  | CDR3 | QAWDSISEEVV | NO: 62 |
|  | Frame 4 | FGGGTKLTV | NO: 63 |
|  | Variable (Frames 1 to 4) | NFMLTQPPSV SVAPGKTASL TCGGYNIGTK SVHWYQQKPG QAPVVVVHDD SDRPSGIPER FSGSNSGTTA TLTISRVEAG DEADYYCQAW DSISEEVVFG GGTKLTV | NO: 64 |
| GPD32 | Frame 1 | SELTQDPAVSVALGQTVRITC | 74 |
|  | CDR1 | QGDSLRSYYAS | 75 |
|  | Frame 2 | WYQQKPGQAPVLVI | 76 |
|  | CDR2 | YGKNNRPS | 77 |
|  | Frame 3 | GIPDRFSGSSSGNTASLT ITGAQAEDEADYYC | 78 |
|  | CDR3 | NSRDSSGIHLV | 79 |
|  | Frame 4 | FGGGTKLTVL | 80 |
|  | Variable (Frames 1 to 4) | SELTQDPAVS VALGQTVRIT CQGDSLRSYY ASWYQQKPGQ APVLVIYGKN NRPSGIPDRF SGSSSGNTAS LTITGAQAED EADYYCNSRD SSGIHLVFGG GTKLTVL | 81 |

The GC4, GB1, GB8, GH9, and GPD32 scFvs all contain the same linker sequence GGGGSGGGGSGGGGS set forth in SEQ ID NO: 65.

TABLE 1-4

Summary of Binding Results for Five Unique Human scFvs

| Property | H3 & GPD32 | GC4 | GB1 | GB8 | GH9 |
|---|---|---|---|---|---|
| Binding to GBM sphere cells | 100% | 0-99% | Variable# | Variable# | Variable# |
| Binding to non-sphere GBM cells | Unchanged (100%) | Reduced | Reduced concurrently with CD133 | Reduced concurrently with CD133 | Reduced concurrently with CD133 |

TABLE 1-4-continued

Summary of Binding Results for Five Unique Human scFvs

| Property | H3 & GPD32 | GC4 | GB1 | GB8 | GH9 |
|---|---|---|---|---|---|
| Relationship to CD133+ cells | Cover CD133+ | Cover CD133+ | A subset of CD133+ | A subset of CD133+ | Co-stain w/ CD133+ |
| Target antigen | CD166 | ND | ND | ND | ND |

For Table 1-4, co-staining with CD133 is shown in FIG. 3. Non-sphere GBM cells were derived from sphere cells cultured in differentiation promoting media containing serum. "ND" indicates not determined. Additionally, #: variable binding patterns are shown in Table 1-5.

TABLE 1-5

Binding Patterns of GB1, GB8 and GH9 to GBM Tumor Sphere cells

| GBM Tissues | CD133 Epitope Expression | GB1 | GB8 | GH9 |
|---|---|---|---|---|
| GBMx-1 | 80% | 26% | 23% | 84% |
| GBMx-2 | 50% | 20% | 18% | 55% |
| GBMx-3 | 2% | 2% | 2% | ND |
| GBMx-4 | 0* | ND | ND | 6% |
| GBMx-5 | 3% | 3% | 2% | 4% |
| GBMx-6 | 4% | 4% | ND | 5% |
| GBMx-7 | 15% | 14% | 11% | 20% |
| GBMx-8 | 70% | 42% | 40% | 73% |
| GBMx-9 | 0* | ND | ND | ND |
| GBMh-1 | 0* | ND | ND | ND |
| GBMh-2 | 12% | 10% | 8% | 15% |
| GBMh-3 | 8% | ND | ND | ND |
| GBMh-4 | 3% | 2% | ND | 4% |
| GBMh-5 | 6% | 4% | ND | 6% |

For Table 1-5, the percentage of positive was determined by FACS. For GBMx-1, 2 and 8, GB1 and GB8 stained a subset of CD133 epitope positive cells. "0*" indicates expression levels indistinguishable from that of the control (control isotype-matched mouse IgG stain), and "ND" indicates not done.

Analysis of Co-Expression of scFv-Targeted Antigens and the CD133 Epitope.

Since the selection scheme was designed to capture binders to the CD133 positive fraction of GBM sphere cells, double labeling analysis was used to determine whether the phage antibodies that bind a subset of the cell population bind preferentially to the CD133 positive population. GB8 and GH9 phage antibodies were tested and found to be co-stained with the anti-CD133 epitope mAb (FIG. 3A), whereas very little phage binding to CD133 epitope negative-cells was observed (<1% for GB8 and <6% for GH9). Thus, GB8 and GH9 bind to antigens expressed mainly on the CD133+ subpopulation of GBM tumor spheres, indicating that the original selection scheme described above was successful. Neither GB8 nor GH9 phage antibodies compete with the anti-CD133 epitope mAb for binding (FIG. 3A, no reductions in percentage of CD133-APC positive cells were observed), indicating that these phage antibodies bind to novel epitopes that do not overlap with the widely used CD133 epitopes.

Figure 3A:
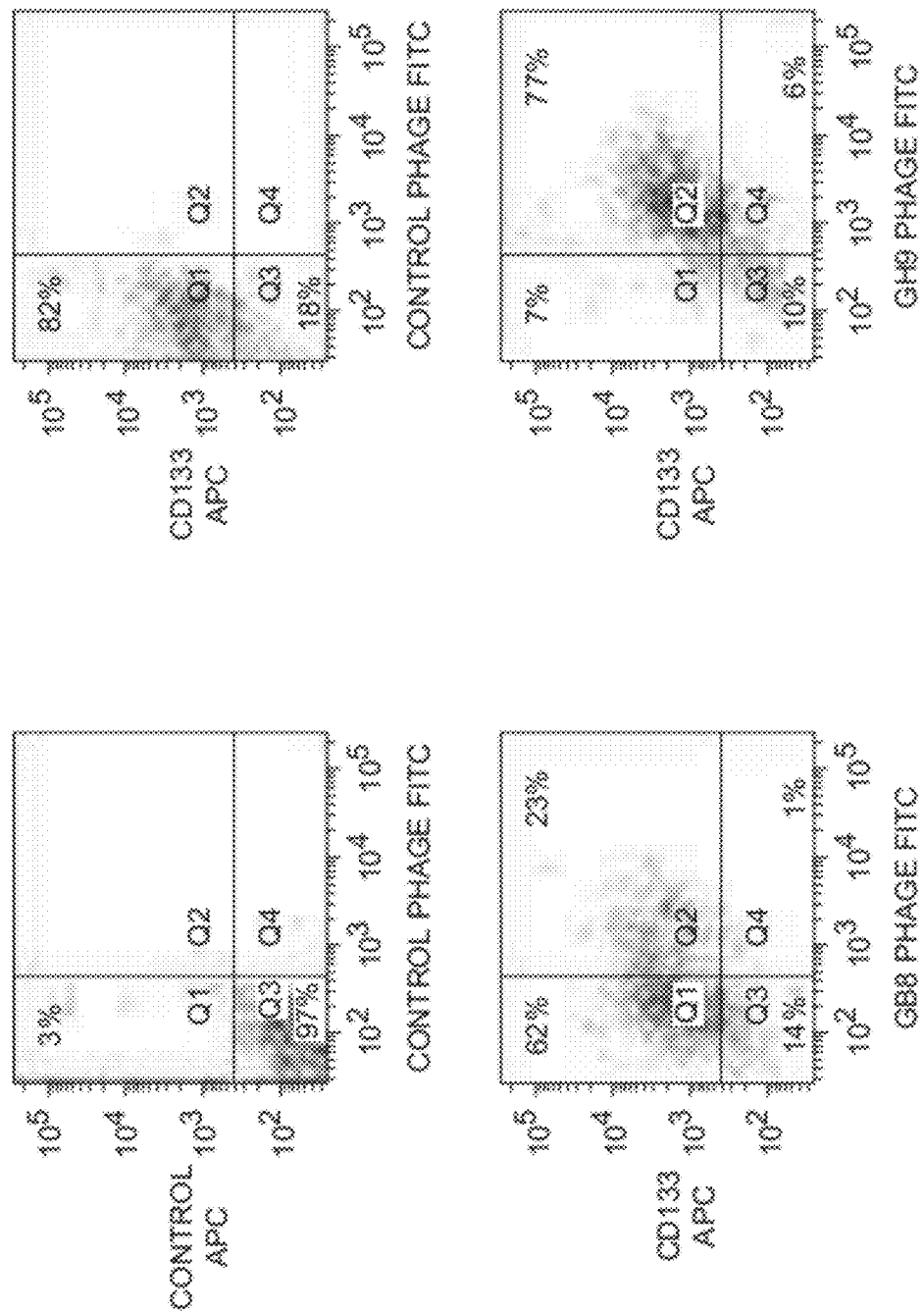
FIG. 3A depicts FITC-labeled phage antibodies and biotin-labeled anti-CD133 mAb were studied on GBM sphere cells. A typical result from studies on GBMx-1 sphere cells is shown. Percentage of total cells is indicated for each quadrant.
Figure 3B:
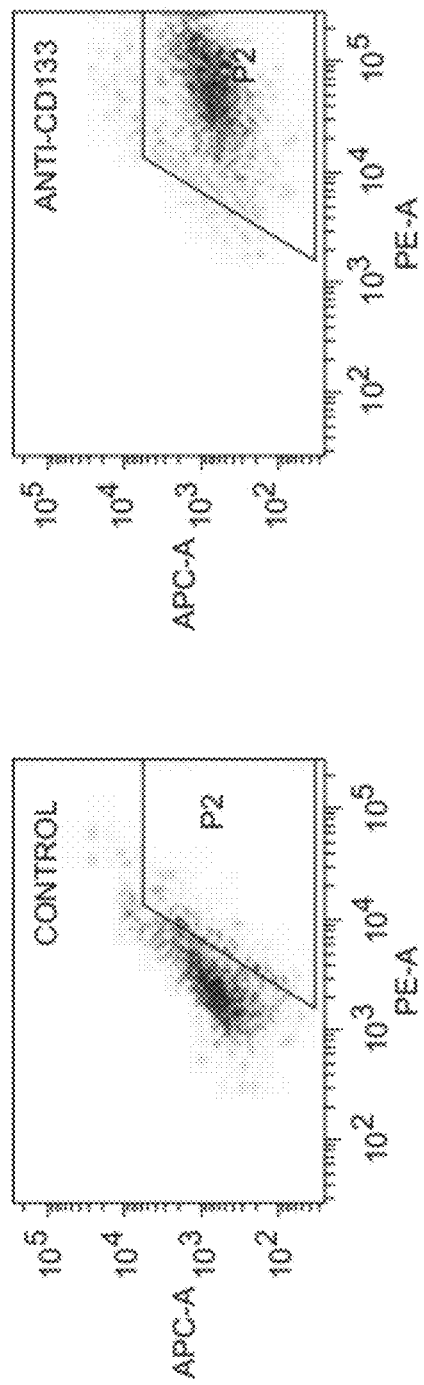
FIG. 3B shows that Caco-2 cells express high levels of CD133. PE-conjugated control mouse IgG and anti-CD133 mAb were incubated with Caoa-2 cells and binding detected by FACS.
Figure 3C:
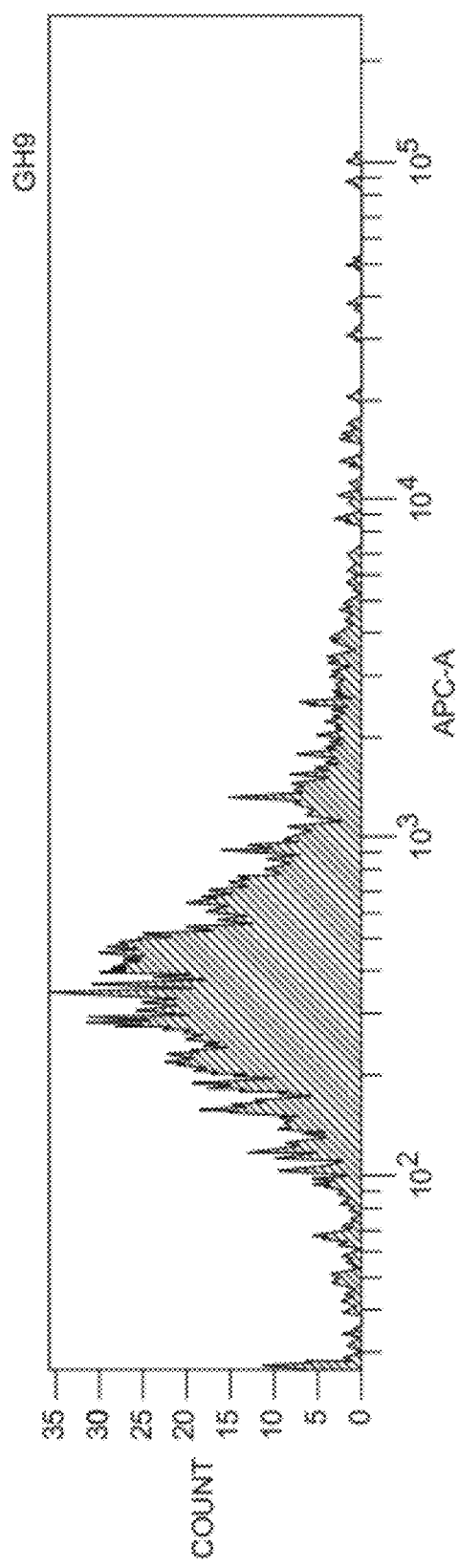
FIG. 3C demonstrates that GBM sphere-targeting phage do not bind to CD133-expressing Caco-2 cells. Four tumor sphere cell-targeting phage (GB1, GB8, GH9 and GC4) were tested. Negative control: a non-binding phage. Positive control: a Caco-2 binding phage preparation.
Figure 3C:
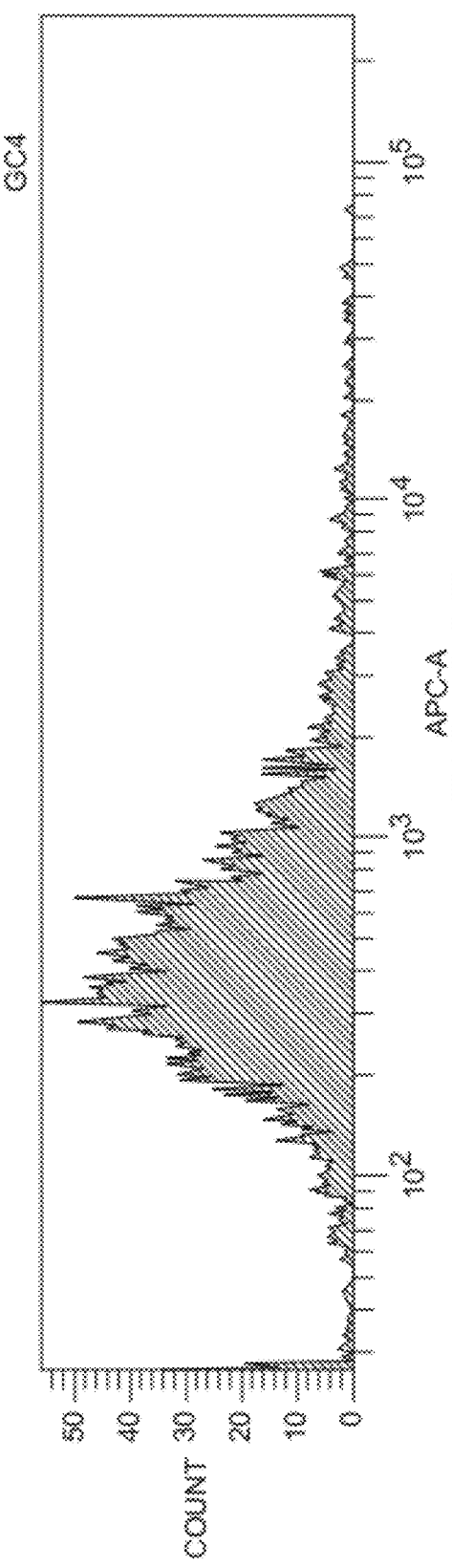
Figure 3D:
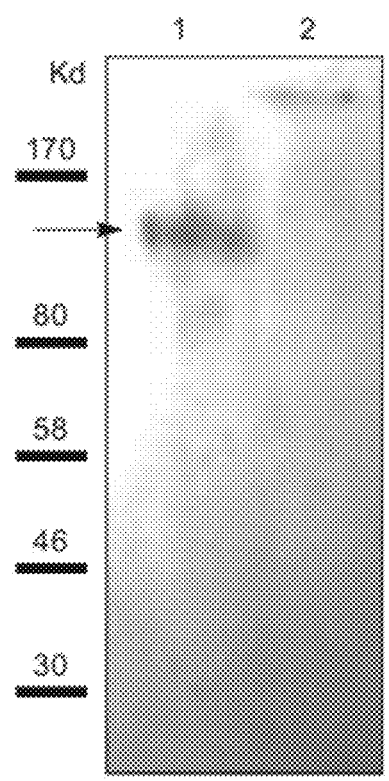
FIG. 3D depicts the results of antibody immunoprecipitation of Caco-2 lysates. Lane 1: immunoprecipitation with anti-CD133 mAb. Lane 2: immunoprecipitation with the GC4 antibody. All immunoprecipitation products were analyzed on a SDS-PAGE gel followed by Western blot with anti-CD133 antibody and horseradish peroxidase-conjugated anti-mouse secondary antibody. Arrow indicates CD133. Molecular weights (kd) are indicated.

To further determine if the identified scFvs bind to CD133 via a different epitope, binding of scFvs to Caco-2 cell line that expresses a high level of CD133 were studied (FIG. 3B). As shown in FIG. 3C, none of the identified scFvs bound to Caco-2 cells, while the positive control anti-CD133 antibody bound strongly to Caco-2 cells. Immunoprecipitation studies were also performed, and the results show that the identified scFvs do not pull down the CD133 molecule, while the positive control antibody does (FIG. 3D). This result is consistent with results of the FACS analysis. Accordingly, it was concluded that the newly identified scFvs do not bind to CD133.

Phage Antibodies Target Antigens Preferentially Associated with Tumor Sphere Cells Grown in Selective Media.

Figure 4A:
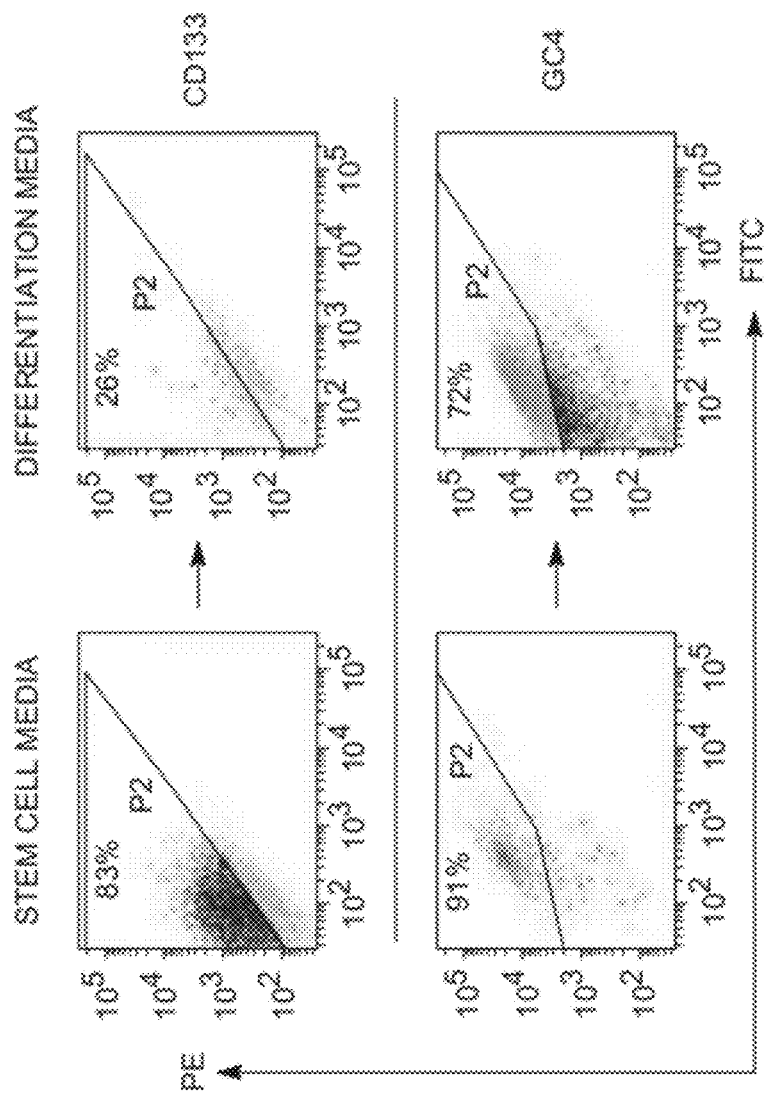
FIG. 4A shows concurrent down-regulation of the CD133 and the phage-bound epitopes. FACS analysis of the expression of the CD133 epitope (top panels) and the antigen bound by the GC4 phage antibody (bottom panels). Concurrent down-regulations were observed when GBM sphere cells were removed from TSFM and cultured in media that promotes differentiation.
Figure 4B:
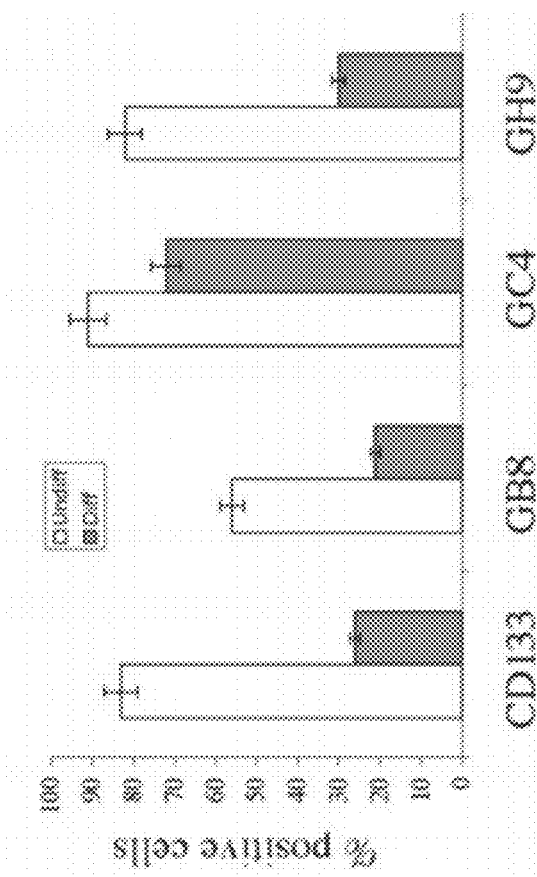
FIG. 4B depicts the quantification of binding status of the anti-CD133 epitope mAb and phage antibodies to GBM tumor sphere cells cultured in TSFM that promote maintenance of the undifferentiated state (Undiff) and non-selective media that promote differentiation (Diff). Experiments were done in triplicates and standard deviations are shown. *, P<0.05.

To test if antigens bound by phage antibodies are preferentially expressed by GBM cells growing in restrictive media as tumor sphere cells, expression of the CD133 epitope and scFv-targeted antigens by GBM cells grown in selective media was compared to GBM cells grown on non-selective media. Concurrent down-regulation of the CD133 epitope and phage antibody-bound epitopes for all the scFvs tested (FIGS. 4A and 4B) was observed. These results indicate that these phage antibody-targeted antigens are preferentially associated with GBM tumor sphere cells growing in selective media.

Antibody Internalization by GBM Tumor Sphere Cells.

Figure 5:
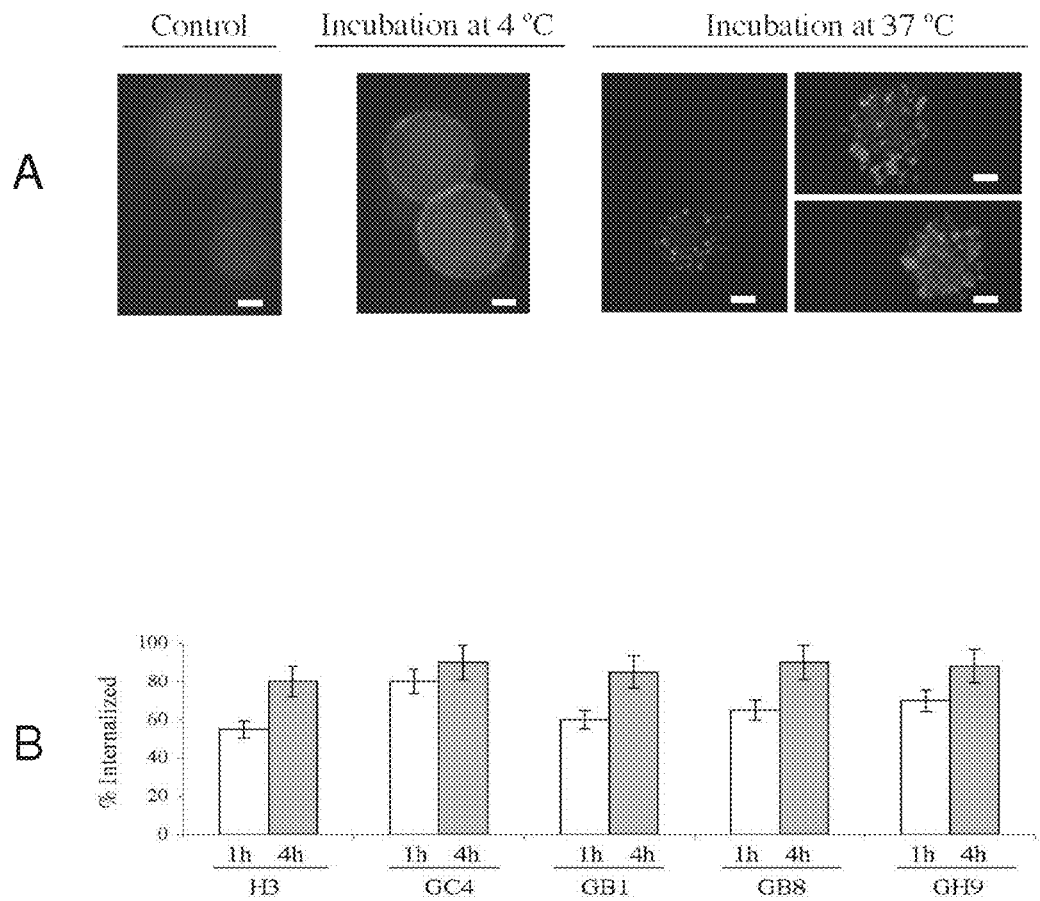
FIG. 5 depicts the internalization by GBM tumor sphere cells.

Phage antibodies were selected for internalizing functions with the goal of developing potential tumor stem cell-targeted therapies based on intracellular delivery strategies. To confirm the internalizing function of selected scFvs, scFvs were labeled with quantum dots (Q-dot 655) and cellular uptake was visualized by fluorescence microscopy. Results from an experiment utilizing the GC4 scFv is shown in FIG. 5A. When incubation was at 4° C., the GC4 scFv was found to bind to the surface of GBM sphere cells. When incubation was at 37° C., which permits receptor-mediated endocytosis, the GC4 scFv was efficiently internalized (FIG. 5A) into intracellular compartments. To rule out potential Q-dot labeling artifacts, the experiment was repeated with FITC-labeled scFvs and the same results were obtained.

To quantify the internalization efficiency, the cell-associated phage antibodies before treatment were compared to antibodies after treatment with a low pH buffer that strips off surface-bound non-internalized phage antibodies. As shown in FIG. 5B, all four scFvs studied were efficiently internalized. Significant internalization was seen as early as 1 h. By 4 h most phage antibodies were internalized (FIG. 5B), demonstrating that our selection strategies were effective at enriching internalizing human scFvs that target the GBM tumor sphere cells.

GC4 scFv Inhibits GBM Tumor Sphere Cell Self-Renewal.

Figure 6:
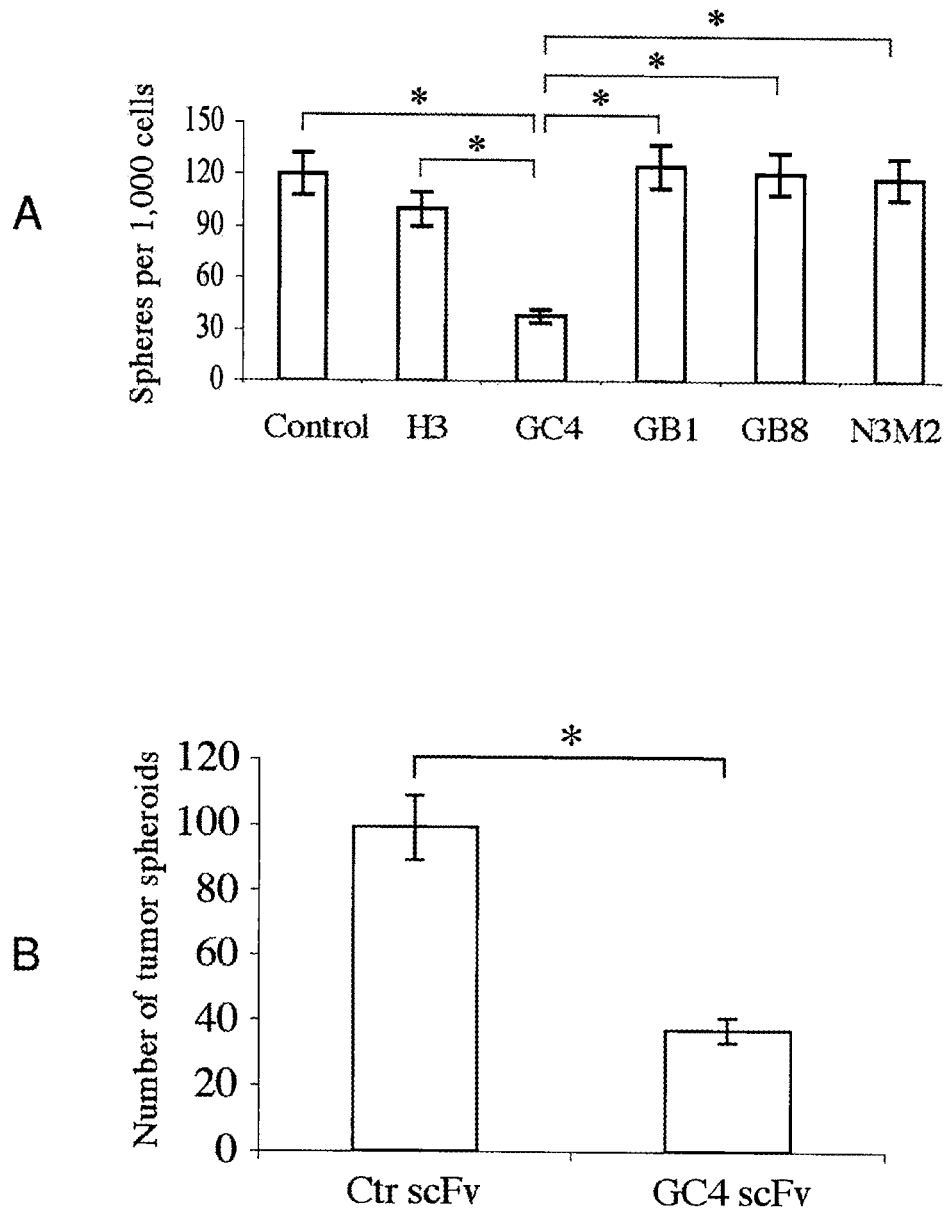
FIG. 6 depicts the results of inhibition of self-renewal of GBM tumor sphere cells.

The ability of the scFvs to inhibit tumor sphere self-renewal was then tested. Affinity-purified recombinant scFvs were incubated with dissociated GBM tumor sphere cells for 7 days, and the efficiency of clonal expansion was determined. The GC4 scFv caused a significant inhibition of GBM sphere growth in vitro (FIG. 6A) suggesting that it modulates the activity of a cell surface antigen that plays a significant role in GBM tumor sphere cell self-renewal. None of the other scFvs tested showed inhibitory effects under identical conditions (FIG. 6A). To test for non-specific cell toxicity, the effect of the GC4 scFv on cell lines that were not bound by this scFv (SKOV3 and PC3, see Table 1-6) was studied. No inhibition was observed in these control experiments.

TABLE 1-6

Binding Specificity of the GC4 scFv

| Cell lines | Binding |
|---|---|
| Tumor cell lines: | |
| Du-145 (metastatic prostate tumor) | + |
| PC3 (metastatic prostate tumor) | − |
| PC3M (metastatic prostate tumor) | − |

TABLE 1-6-continued

Binding Specificity of the GC4 scFv

| Cell lines | Binding |
|---|---|
| SKOV3 (ovarian tumor) | – |
| OVCAR3 (ovarian tumor) | – |
| Caco2 (colon carcinoma) | – |
| U87 MG (glioblastoma-astrocytoma) | – |
| MIA CaPa2 (pancreatic tumor) | – |
| Colo357 (pancreatic tumor) | – |
| L3.3 (pancreatic tumor) | – |
| L3.6PL (pancreatic tumor) | – |
| SW1990 (pancreatic tumor) | – |
| CFPAC1 (pancreatic tumor) | – |
| M28 (mesothelioma) | – |
| VAMT-1 (mesothelioma) | – |
| Non-tumorgenic cell line: | |
| BPH-1 (benign prostatic hyperplasia) | – |

For Table 1-6, biotin-labeled GC4 scFvs were tested for binding to a panel of human cell lines (all were tumor lines, except for BPH-1) by FACS. "+" indicates binding and "–" indicated lack of significant binding. Du-145 cells were derived from brain metastasis of prostate tumor.

To further determine if GC4 scFv is capable of inhibiting the growth of established GBM tumor spheres, monodispersed GBM cells were grown in TSFM to obtain tumor spheroids, and then treated with recombinant GC4 scFv (100 μg/ml). As shown in FIG. 6B, treatment with the GC4, but not the control scFv, significantly reduced the growth of established tumor spheres.

GC4 IgG1 Inhibits Proliferation of GBM Tumor Sphere Cells.

Figure 7A:
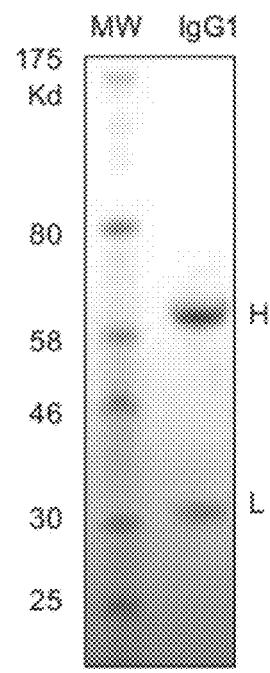
FIG. 7A depicts the production of recombinant GC4 IgG. H: heavy chain. L: light chain. MW: molecular weight.
Figure 7B:
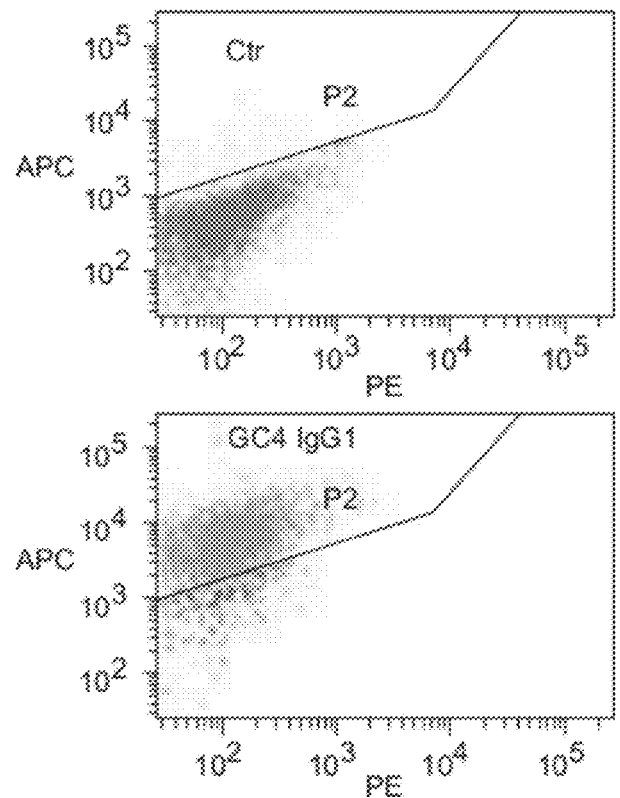
FIG. 7B shows the results of a quality control study confirming that the GC4 scFv-derived IgG1 retains the ability to bind GBM sphere cells. Ctr: a non-binding human IgG1.
Figure 7C:
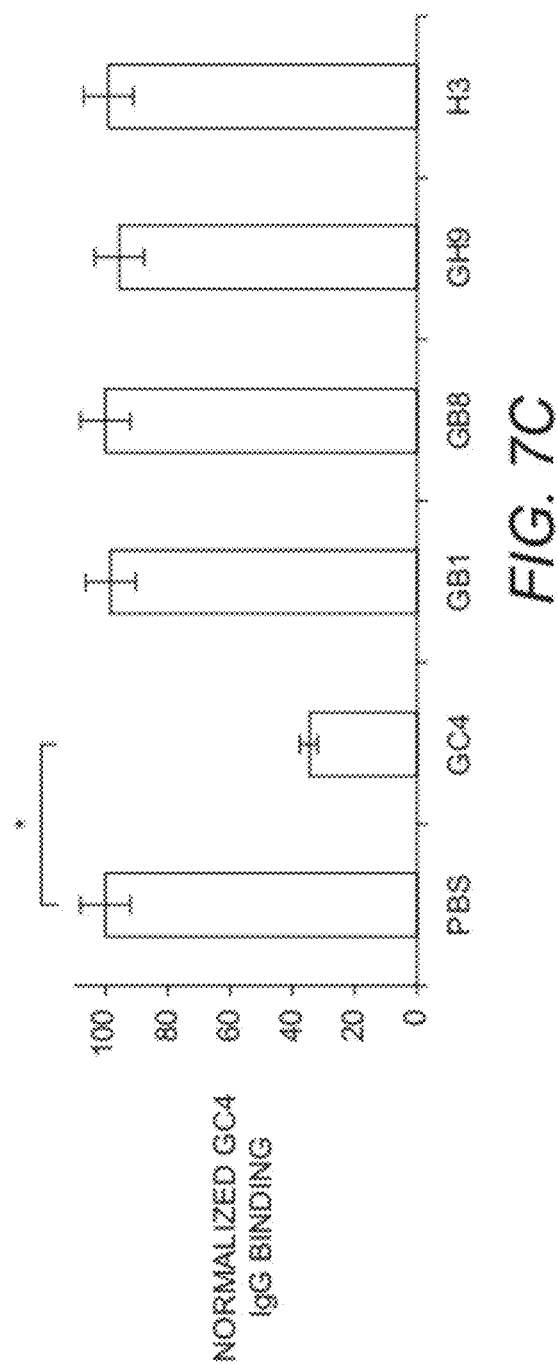
FIG. 7C demonstrates that recombinant GC4 IgG1 retains binding specificity of the parental scFv. FACS analysis was performed to determine binding of GC4 IgG1 (1 μg/ml) in the presence of the parental GC4 or four other scFvs (50 μg/ml each). Binding was detected by fluorescently labeled anti-human IgG antibody. Normalized mean fluorescence intensities were used to compare binding results. Error bars indicate standard deviations of duplicated experiments. *, $P<0.05$.

Given that the GC4 scFv inhibits proliferation of GBM tumor sphere cells, it was thought that full-length human GC4 IgG1 would also inhibit proliferation. Thus, a full-length human GC4 IgG1 was also developed to test in vivo applications. Using the VH and VL sequences from the GC4 scFv, the GC4 IgG1 was constructed in a mammalian expression vector. CHO-DG44 cells were then transformed with the vector, resulting in production of full-length recombinant human GC4 IgG1 in the cells. Analysis of purified IgG1 by reducing SDS-PAGE showed heavy and light chains with appropriate sizes (FIG. 7A). For quality control, binding of the recombinant GC4 IgG1 to GBM tumor sphere cells was also tested and confirmed (FIG. 7B). In addition, the GC4 IgG competed specifically with the parent GC4 scFv for binding to GBM sphere cells (FIG. 7C), demonstrating that the IgG and the scFv have the same specificity, consistent with previous experience with recombinant IgG development (34). Additionally, cell binding affinity was also measured by FACS, and it was found that the GC4 IgG1 binds with greater affinity than the parental scFv. Specifically, the binding constant measured at RT is 79 nM for IgG1 (FIG. 7D) vs. 222 nM for scFv (FIG. 7E). Inhibitory effects of the GC4 IgG1 on GBM tumor sphere cells grown in selective media were also tested. Like the parental GC4 scFv, recombinant GC4 IgG1 inhibited self-renewal of GBM tumor sphere cells (about 60% inhibition, similar to that of the GC4 scFv).

Figure 8:
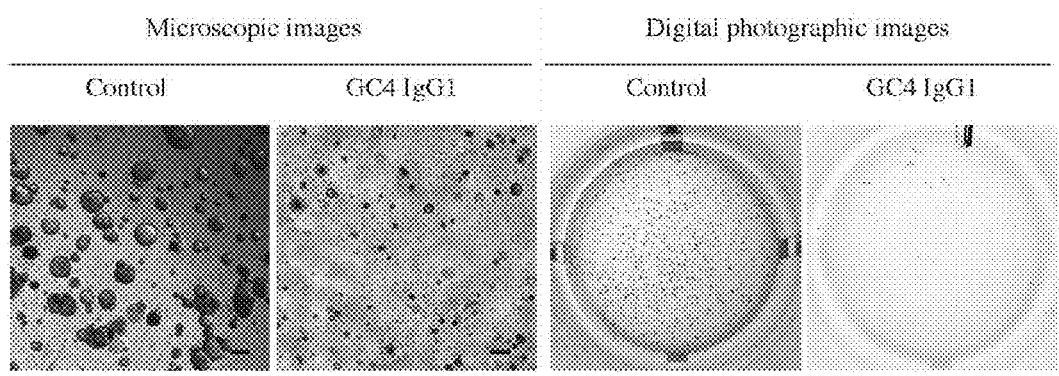
FIG. 8 shows that GC4 IgG1 inhibits colony formation of GBM cells in the soft agar assay. Both microscopic and digital photographic images of the GC4 and control IgG1-treated wells are shown. Scale bar, 250 μm.

To determine if this inhibitory effect is also applicable to GBM cells grown under non-selective culture conditions, GBM cells cultured in non-selective media were treated with the GC4 IgG1, and cloning efficiencies were measured using the soft agar assay. As shown in FIG. 8, the GC4 IgG1 inhibited the clonogenic activity of GBM cells. Compared to controls, the GC4 IgG1-treated GBM cells formed significantly fewer colonies. Moreover, the colonies formed by the GC4 IgG1-treated cells are significantly smaller than those formed by cells treated with the control IgG (FIG. 8). This experiment was repeated on GBM cells derived from five independent cases. Inhibitory effects were observed in four of these cases. Again, no inhibitory effects were observed on cell lines to which the GC4 antibody does not bind (SKOV3 and PC3; non-binding cells are listed in Table 1-6). These results demonstrate that GC4 human IgG1 is a potent inhibitor of GBM cell proliferation in non-selective media.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

REFERENCES

1. Krex et al. Long-term survival with glioblastoma multiforme. Brain 2007; 130:2596-606.
2. Nicholas, Glioblastoma multiforme: evidence-based approach to therapy. Expert Rev Anticancer Ther 2007; 7:S23-7.
3. Benitez et al., Conventional and gene therapy strategies for the treatment of brain tumors. Curr Med Chem 2008; 15:729-42.
4. Chang et al., Radiotherapy and radiosensitizers in the treatment of glioblastoma multiforme. Clin Adv Hematol Oncol 2007; 5:894-902, 07-15.
5. Reardon et al., The emerging role of anti-angiogenic therapy for malignant glioma. Curr Treat Options Oncol 2008; 9:1-22.
6. Reya et al., Stem cells, cancer, and cancer stem cells. Nature 2001; 414:105-11.
7. Pardal et al., Applying the principles of stem-cell biology to cancer. Nat Rev Cancer 2003; 3:895-902.
8. Dalerba et al., Cancer stem cells: models and concepts. Annu Rev Med 2007; 58:267-84.
9. Eyler et al., Survival of the fittest: cancer stem cells in therapeutic resistance and angiogenesis. J Clin Oncol 2008; 26:2839-45.
10. Jiang et al., Chronic myeloid leukemia stem cells possess multiple unique features of resistance to BCR-ABL targeted therapies. Leukemia 2007; 21:926-35.
11. Sims et al., Origins of breast cancer subtypes and therapeutic implications. Nat Clin Pract Oncol 2007; 4:516-25.
12. Singh et al., Identification of a cancer stem cell in human brain tumors. Cancer Res 2003; 63:5821-8.
13. Singh et al., Cancer stem cells in nervous system tumors. Oncogene 2004; 23:7267-73.
14. Singh et al., Identification of human brain tumour initiating cells. Nature 2004; 432:396-401.
15. Yuan et al., Isolation of cancer stem cells from adult glioblastoma multiforme. Oncogene 2004; 23:9392-400.
16. Bidlingmaier et al., The utility and limitations of glycosylated human CD133 epitopes in defining cancer stem cells. J Mol Med 2008; 86:1025-32.
17. Lee et al., Tumor stem cells derived from glioblastomas cultured in bFGF and EGF more closely mirror the phenotype and genotype of primary tumors than do serum-cultured cell lines. Cancer Cell 2006; 9:391-403.

18. Nielsen et al., Internalizing antibodies and targeted cancer therapy: direct selection from phage display libraries. Pharm. Sci. Technol. Today 2000; 3:282-91.
19. Liu, Exploring cell type-specific internalizing antibodies for targeted delivery of siRNA. Brief Funct Genomic Proteomic 2007; 6:112-9.
20. Poul et al., Selection of tumor-specific internalizing human antibodies from phage libraries. J Mol Biol 2000; 301:1149-61.
21. Becerril et al., Toward selection of internalizing antibodies from phage libraries. Biochem Biophys Res Commun 1999; 255:386-93.
22. Liu et al., Mapping tumor epitope space by direct selection of single-chain Fv antibody libraries on prostate cancer cells. Cancer Res 2004; 64:704-10.
23. Roth et al., Anti-CD166 single chain antibody-mediated intracellular delivery of liposomal drugs to prostate cancer cells. Mol Cancer Ther 2007; 6:2737-46.
24. An et al., Targeted drug delivery to mesothelioma cells using functionally selected internalizing human single-chain antibodies. Mol Cancer Ther 2008; 7:569-78.
25. Bidlingmaier et al., Identification of MCAM/CD146 as the target antigen of a human monoclonal antibody that recognizes both epithelioid and sarcomatoid types of mesothelioma. Cancer Res 2009; 69:1570-7.
26. Ruan et al., Identification of clinically significant tumor antigens by selecting phage antibody library on tumor cells in situ using laser capture microdissection. Mol Cell Proteomics 2006; 5:2364-73.
27. Giannini et al., Patient tumor EGFR and PDGFRA gene amplifications retained in an invasive intracranial xenograft model of glioblastoma multiforme. Neuro Oncol 2005; 7:164-76.
28. Kabos et al., Generation of neural progenitor cells from whole adult bone marrow. Exp Neurol 2002; 178:288-93.
29. Westhoff et al., Identification of a novel switch in the dominant forms of cell adhesion-mediated drug resistance in glioblastoma cells. Oncogene 2008.
30. O'Connell et al., Phage versus phagemid libraries for generation of human monoclonal antibodies. J Mol Biol 2002; 321:49-56.
31. Sheets et al., Efficient construction of a large nonimmune phage antibody library: the production of high-affinity human single-chain antibodies to protein antigens. Proc Natl Acad Sci USA 1998; 95:6157-62.
32. Liu and Marks, Applying phage antibodies to proteomics: selecting single chain Fv antibodies to antigens blotted on nitrocellulose. Anal Biochem 2000; 286:119-28.
33. Liu et al., Towards proteome-wide production of monoclonal antibody by phage display. J Mol Biol 2002; 315: 1063-73.
34. Liu et al., Recombinant full-length human IgG1s targeting hormone-refractory prostate cancer. J Mol Med 2007; 85:1113-23.
35. Nowakowski et al., Potent neutralization of botulinum neurotoxin by recombinant oligoclonal antibody. Proc Natl Acad Sci USA 2002; 99:11346-50.
36. Dallas et al., Chemoresistant colorectal cancer cells, the cancer stem cell phenotype, and increased sensitivity to insulin-like growth factor-I receptor inhibition. Cancer Res 2009; 69:1951-7.
37. Pandita et al., Contrasting in vivo and in vitro fates of glioblastoma cell subpopulations with amplified EGFR. Genes Chromosomes Cancer 2004; 39:29-36.
38. Li et al., Identification of pancreatic cancer stem cells. Cancer Res 2007; 67:1030-7.
39. Weiner et al., Monoclonal antibodies for cancer immunotherapy. Lancet 2009; 373:1033-40.
40. Adams and Weiner, Monoclonal antibody therapy of cancer. Nat Biotechnol 2005; 23:1147-57.
41. Altaner, Glioblastoma and stem cells. Neoplasma 2008; 55:369-74.
42. Thurber et al., Antibody tumor penetration: transport opposed by systemic and antigen-mediated clearance. Adv Drug Deliv Rev 2008; 60:1421-34.
43. Adams et al., High affinity restricts the localization and tumor penetration of single-chain fv antibody molecules. Cancer Res 2001; 61:4750-5.
44. Adams et al., Avidity-mediated enhancement of in vivo tumor targeting by single-chain Fv dimers. Clin Cancer Res 2006; 12:1599-605.
45. Juweid et al., Micropharmacology of monoclonal antibodies in solid tumors: direct experimental evidence for a binding site barrier. Cancer Res 1992; 52:5144-53.
46. Ackerman et al., Effect of antigen turnover rate and expression level on antibody penetration into tumor spheroids. Mol Cancer Ther 2008; 7:2233-40.
47. Sundaresan et al., [124]I-labeled engineered anti-CEA minibodies and diabodies allow high-contrast, antigen-specific small-animal PET imaging of xenografts in athymic mice. J Nucl Med 2003; 44:1962-9.
48. Calabrese et al. A perivascular niche for brain tumor stem cells. Cancer Cell 2007; 11:69-82.
49. Veeravagu et al., The cancer stem cell-vascular niche complex in brain tumor formation. Stem Cells Dev 2008; 17:859-67.
50. He et al., Targeting prostate cancer cells in vivo using a rapidly internalizing novel human single-chain antibody fragment. J Nucl Med 2010; 51:427-32.
* Zhu et al., Identification of internalizing human single-chain antibodies targeting brain tumor sphere cells, Mol Cancer Ther, 9:2131-2141, 2010.

We claim:

1. An isolated antibody that binds specifically to glioblastoma multiforme (GBM) tumor sphere cells, wherein the anti-GBM antibody comprises an antigen binding site that comprises:
   (a) a heavy chain comprising (i) complementarity determining region (CDR)-H1 comprising SEQ ID NO: 2, (ii) CDR-H2 comprising SEQ ID NO: 4, and (iii) CDR-H3 comprising SEQ ID NO: 6, and a light chain comprising (iv) CDR-L1 comprising SEQ ID NO: 34, (v) CDR-L2 comprising SEQ ID NO: 36, and (vi) CDR-L3 comprising SEQ ID NO: 38;
   (b) a heavy chain comprising (i) complementarity determining region (CDR)-H1 comprising SEQ ID NO: 10, (ii) CDR-H2 comprising SEQ ID NO: 12, and (iii) CDR-H3 comprising SEQ ID NO: 14, and a light chain comprising (iv) CDR-L1 comprising SEQ ID NO: 42, (v) CDR-L2 comprising SEQ ID NO: 44, and (vi) CDR-L3 comprising SEQ ID NO: 46;
   (c) a heavy chain comprising (i) complementarity determining region (CDR)-H1 comprising SEQ ID NO: 18, (ii) CDR-H2 comprising SEQ ID NO: 20, and (iii) CDR-H3 comprising SEQ ID NO: 22, and a light chain comprising (iv) CDR-L1 comprising SEQ ID NO: 50, (v) CDR-L2 comprising SEQ ID NO: 52, and (vi) CDR-L3 comprising SEQ ID NO: 54;
   (d) a heavy chain comprising (i) complementarity determining region (CDR)-H1 comprising SEQ ID NO: 26, (ii) CDR-H2 comprising SEQ ID NO: 28, and (iii) CDR-H3 comprising SEQ ID NO: 30, and a light chain comprising (iv) CDR-L1 comprising SEQ ID NO: 58, (v) CDR-L2 comprising SEQ ID NO: 60, and (vi) CDR-L3 comprising SEQ ID NO: 62; or
   (e) a heavy chain comprising (i) complementarity determining region (CDR)-H1 comprising SEQ ID NO: 67, (ii) CDR-H2 comprising SEQ ID NO: 69, and (iii) CDR-H3 comprising SEQ ID NO: 71, and a light chain comprising (iv) CDR-L1 comprising SEQ ID NO: 75, (v) CDR-L2 comprising SEQ ID NO: 77, and (vi) CDR-L3 comprising SEQ ID NO: 79.

2. The anti-GBM antibody of claim 1, wherein the antigen binding site comprises the heavy chain variable region of SEQ ID NO: 8, and the light chain variable region of SEQ ID NO: 40.

3. The anti-GBM antibody of claim 1, wherein the antigen binding site comprises the heavy chain variable region of SEQ ID NO: 16, and the light chain variable region of SEQ ID NO: 48.

4. The anti-GBM antibody of claim 1, wherein the antigen binding site comprises the heavy chain variable region of SEQ ID NO: 24, and the light chain variable region of SEQ ID NO: 56.

5. The anti-GBM antibody of claim 1, wherein the antigen binding site comprises the heavy chain variable region of SEQ ID NO: 32, and the light chain variable region of SEQ ID NO: 64.

6. The anti-GBM antibody of claim 1, wherein the antigen binding site comprises the heavy chain variable region of SEQ ID NO: 73, and the light chain variable region of SEQ ID NO: 81.

7. An isolated anti-GBM antibody that competes for binding to glioblastoma multiforme (GBM) tumor sphere cells with the anti-GBM antibody of claim 1.

8. The anti-GBM antibody of claim 1, wherein the antibody inhibits proliferation of GBM tumor sphere cells.

9. The anti-GBM antibody of claim 1, wherein the antibody is an antibody fragment.

10. The anti-GBM antibody of claim 9, wherein the fragment is an Fab, F(ab')$_2$, Fv or Sfv fragment.

11. The anti-GBM antibody of claim 1, wherein the antibody is a full-length human immunoglobulin g (IgG) antibody.

12. The anti-GBM antibody of claim 1, wherein the antibody is coupled to one of the group consisting of a detectable marker, and a chemotherapeutic agent.

13. The anti-GBM antibody of claim 12, wherein the antibody is coupled to a detectable marker selected from the group consisting of a radioisotope, a metal chelator, an enzyme, a fluorescent compound, a bioluminescent compound, and a chemiluminescent compound.

14. The anti-GBM antibody of claim 13, wherein the radioisotope comprises one of the group consisting of $^{212}$Bi, $^{131}$I, $^{131}$In, $^{90}$Y, $^{186}$Re, $^{211}$At, $^{125}$I, $^{188}$Re, $^{153}$Sm, $^{213}$Bi, $^{32}$P, and $^{177}$Lu.

15. The anti-GBM antibody of claim 12, wherein the antibody is coupled to a chemotherapeutic agent.

16. A method for characterizing a biopsy sample from a patient, comprising:
   a) contacting the sample with the anti-GBM antibody of claim 1;
   b) detecting the binding of the anti-GBM antibody to cells of the sample; and
   c) characterizing the sample as containing cells expressing an antigen bound by the anti-GBM antibody when binding is detected.

17. The method of claim 16, wherein the biopsy sample is from a brain tumor.

18. A method for treating a cancer patient having tumor cells that express an antigen bound by an anti-GBM antibody, comprising:
   A) providing a composition comprising the anti-GBM antibody comprising an antigen binding site that comprises
   (a) a heavy chain comprising (i) complementarity determining region (CDR)-H1 comprising SEQ ID NO: 2, (ii) CDR-H2 comprising SEQ ID NO: 4, and (iii) CDR-H3 comprising SEQ ID NO: 6, and a light chain comprising (iv) CDR-L1 comprising SEQ ID NO: 34, (v) CDR-L2 comprising SEQ ID NO: 36, and (vi) CDR-L3 comprising SEQ ID NO: 38;
   (b) a heavy chain comprising (i) complementarity determining region (CDR)-H1 comprising SEQ ID NO: 10, (ii) CDR-H2 comprising SEQ ID NO: 12, and (iii) CDR-H3 comprising SEQ ID NO: 14, and a light chain comprising (iv) CDR-L1 comprising SEQ ID NO: 42, (v) CDR-L2 comprising SEQ ID NO: 44, and (vi) CDR-L3 comprising SEQ ID NO: 46;
   (c) a heavy chain comprising (i) complementarity determining region (CDR)-H1 comprising SEQ ID NO: 18, (ii) CDR-H2 comprising SEQ ID NO: 20, and (iii) CDR-H3 comprising SEQ ID NO: 22, and a light chain comprising (iv) CDR-L1 comprising SEQ ID NO: 50, (v) CDR-L2 comprising SEQ ID NO: 52, and (vi) CDR-L3 comprising SEQ ID NO: 54;
   (d) a heavy chain comprising (i) complementarity determining region (CDR)-H1 comprising SEQ ID NO: 26, (ii) CDR-H2 comprising SEQ ID NO: 28, and (iii) CDR-H3 comprising SEQ ID NO: 30, and a light chain comprising (iv) CDR-L1 comprising SEQ ID NO: 58, (v) CDR-L2 comprising SEQ ID NO: 60, and (vi) CDR-L3 comprising SEQ ID NO: 62; or
   (e) a heavy chain comprising (i) complementarity determining region (CDR)-H1 comprising SEQ ID NO: 67, (ii) CDR-H2 comprising SEQ ID NO: 69, and (iii) CDR-H3 comprising SEQ ID NO: 71, and a light chain comprising (iv) CDR-L1 comprising SEQ ID NO: 75, (v) CDR-L2 comprising SEQ ID NO: 77, and (vi) CDR-L3 comprising SEQ ID NO: 79; and
   B) administering to the patient the composition in an amount effective to inhibit proliferation of the tumor cells of the patient.

19. The method of claim 18, wherein the tumor cells are glioblastoma multiforme (GBM) tumor cells.

20. The method of claim 18, wherein the composition is administered intravenously or intracranially.

21. The method of claim 18, further comprising administering an effective amount of an additional chemotherapeutic agent to the patient.

22. The method of claim 18, further comprising one or both of surgically resecting the tumor cells and administering radiation therapy.

* * * * *

SEQUENCE LISTING

<160> NUMBER OF SEQ ID NOS: 81

<210> SEQ ID NO 1
<211> LENGTH: 30
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Gly
            20                  25                  30
```

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

```
Thr Tyr Asp Met Ser
 1               5
```

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

```
Trp Val Arg Gln Ala Pro Gly Lys Gly Leu Glu Trp Val Ser
 1               5                  10
```

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

```
Gly Ile Ser Gly Ser Gly Gly Ser Thr Tyr Tyr Ala Asp Ser Val Lys
 1               5                  10                  15

Gly
```

<210> SEQ ID NO 5
<211> LENGTH: 32
<212> TYPE: PRT
<213> ORGANISM: Artificial Sequence
<220> FEATURE:
<223> OTHER INFORMATION: Synthetic Construct

<400> SEQUENCE: 5

```
Arg Phe Thr Ile Ser Arg Asp Asn Ser Lys Asn Thr Val Tyr Leu Gln
 1               5                  10                  15

Met Asn Ser Leu Arg Val Glu Asp Thr Ala Val Tyr Tyr Cys Ala Arg
            20                  25                  30
```

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

```
Gly Gly Trp Tyr Ser Asp Asn
 1               5
```

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Trp Gly Gln Gly Thr Leu Val Thr Val Ser Ser
1               5                   10

<210> SEQ ID NO 8
<211> LENGTH: 116
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Asp Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Val Glu Asp Thr Ala Val Tyr Tyr Cys
                85                  90                  95

Ala Arg Gly Gly Trp Tyr Ser Asp Asn Trp Gly Gln Gly Thr Leu Val
            100                 105                 110

Thr Val Ser Ser
        115

<210> SEQ ID NO 9
<211> LENGTH: 30
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Asn Ala Trp Met Asn
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 11

Trp Val Arg Gln Ala Pro Gly Lys Gly Leu Glu Trp Val Gly
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Synthetic Construct

<400> SEQUENCE: 12

Arg Ile Lys Ser Lys Thr Asp Gly Gly Thr Thr Asp Tyr Ala Ala Pro
1               5                   10                  15

Val Asn Gly

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Ser Cys Thr Thr
            20                  25                  30

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Glu Asn Trp Gly Ser Val Asn
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Trp Gly Gln Gly Thr Leu Val Thr Val Ser Ser
1               5                   10

<210> SEQ ID NO 16
<211> LENGTH: 118
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
```

```
                35                  40                  45
Gly Arg Ile Lys Ser Lys Thr Asp Gly Gly Thr Thr Asp Tyr Ala Ala
         50                  55                  60

Pro Val Asn Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Ser Cys Thr Thr Glu Asn Trp Gly Ser Val Asn Trp Gly Gln Gly Thr
            100                 105                 110

Leu Val Thr Val Ser Ser
        115

<210> SEQ ID NO 17
<211> LENGTH: 30
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser
             20                  25                  30

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Asn Tyr Ala Leu Thr
  1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Trp Val Arg Gln Ala Pro Gly Lys Gly Leu Glu Trp Val Ser
  1               5                  10

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Ala Ile Ser Gly Ser Gly Gly Ser Thr Tyr Tyr Ala Asp Ser Val Lys
  1               5                  10                  15

Gly

<210> SEQ ID NO 21
<211> LENGTH: 32
<212> TYPE: PRT
<213> ORGANISM: Artificial Sequence
```

<220> FEATURE:
<223> OTHER INFORMATION: Synthetic Construct

<400> SEQUENCE: 21

```
Arg Phe Thr Ile Ser Arg Asp Thr Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

```
Gly Gly Tyr Ser Tyr Gly Pro Pro Phe Asp Tyr
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

```
Trp Gly Gln Gly Thr Leu Val Thr Val Ser Ser
1               5                   10
```

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct

<400> SEQUENCE: 24

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Leu Thr Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Ser Tyr Gly Pro Pro Phe Asp Tyr Trp Gly Gln
            100                 105                 110

Gly Thr Leu Val Thr Val Ser Ser
        115                 120
```

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct -continued

<400> SEQUENCE: 25

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Ser Tyr Ser Met Asn
1               5

<210> SEQ ID NO 27
<211> LENGTH: 14
<212> TYPE: PRT
<213> ORGANISM: Artificial Sequence
<220> FEATURE:
<223> OTHER INFORMATION: Synthetic Construct

<400> SEQUENCE: 27

Trp Val Arg Gln Ala Pro Gly Gln Gly Leu Glu Trp Val Ser
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Ser Ile Ser Ser Arg Asn Ser Asp Ile Tyr Tyr Ala Asp Ser Val Arg
1               5                   10                  15

Gly

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Asp Ser Ser Gly Tyr Ser Ser Ser Pro Ser Asp Tyr
1               5                   10

```
<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Trp Gly Gln Gly Thr Leu Val Thr Val Ser Ser
 1               5                  10

<210> SEQ ID NO 32
<211> LENGTH: 121
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Gln Gly Leu Glu Trp Val
        35                  40                  45

Ser Ser Ile Ser Ser Arg Asn Ser Asp Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Gly Tyr Ser Ser Pro Ser Tyr Trp Gly
            100                 105                 110

Gln Gly Thr Leu Val Thr Val Ser Ser
        115                 120

<210> SEQ ID NO 33
<211> LENGTH: 21
<212> TYPE: PRT
<213> ORGANISM: Artificial Sequence
<220> FEATURE:
<223> OTHER INFORMATION: Synthetic Construct

<400> SEQUENCE: 33

Ser Glu Leu Thr Gln Asp Pro Ala Val Ser Val Ala Leu Gly Gln Thr
 1               5                  10                  15

Val Arg Ile Thr Cys
            20

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Gln Gly Gly Ser Leu Arg Ser Tyr Tyr Ala Ser
 1               5                  10

<210> SEQ ID NO 35
<211> LENGTH: 14
<212> TYPE: PRT
```

```
<213> ORGANISM: Artificial Sequence
<220> FEATURE:
<223> OTHER INFORMATION: Synthetic Construct

<400> SEQUENCE: 35

Trp Tyr Gln Gln Lys Pro Gly Gln Ala Pro Leu Leu Val Ile
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Tyr Gly Glu Asn Asn Arg Pro Ser
1               5

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: Synthetic Construct

<400> SEQUENCE: 38

His Ser Arg Asp Ser Ser Gly Asn His Val Val
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Phe Gly Gly Gly Thr Lys Leu Thr Val
1               5

<210> SEQ ID NO 40
<211> LENGTH: 106
<212> TYPE: PRT
<213> ORGANISM: Artificial Sequence
<220> FEATURE:
<223> OTHER INFORMATION: Synthetic Construct

<400> SEQUENCE: 40

Ser Glu Leu Thr Gln Asp Pro Ala Val Ser Val Ala Leu Gly Gln Thr
1               5                   10                  15

Val Arg Ile Thr Cys Gln Gly Gly Ser Leu Arg Ser Tyr Tyr Ala Ser
            20                  25                  30
```

```
Trp Tyr Gln Gln Lys Pro Gly Gln Ala Pro Leu Leu Val Ile Tyr Gly
            35                  40                  45

Glu Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys His Ser Arg Asp Ser Ser Gly Asn His Val
                 85                  90                  95

Val Phe Gly Gly Gly Thr Lys Leu Thr Val
                100                 105

<210> SEQ ID NO 41
<211> LENGTH: 22
<212> TYPE: PRT
<213> ORGANISM: Artificial Sequence
<220> FEATURE:
<223> OTHER INFORMATION: Synthetic Construct

<400> SEQUENCE: 41

Asn Phe Met Leu Thr Gln Pro Pro Ser Val Ser Val Ala Pro Gly Lys
 1               5                  10                  15

Thr Ala Ser Leu Thr Cys
            20

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Tyr Asn Ile Gly Thr Lys Ser Val His
 1               5                  10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Trp Tyr Gln Gln Lys Pro Gly Gln Ala Pro Val Val Val Val
 1               5                  10

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct

<400> SEQUENCE: 44

His Asp Asp Ser Asp Arg Pro Ser
 1               5

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 45

Gly Ile Pro Glu Arg Phe Ser Gly Ser Asn Ser Gly Thr Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Gln Ala Trp Asp Ser Ile Ser Glu Glu Val Val
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Phe Gly Gly Gly Thr Lys Leu Thr Val
1               5

<210> SEQ ID NO 48
<211> LENGTH: 106
<212> TYPE: PRT
<213> ORGANISM: Artificial Sequence
<220> FEATURE:
<223> OTHER INFORMATION: Synthetic Construct

<400> SEQUENCE: 48

Asn Phe Met Leu Thr Gln Pro Pro Ser Val Ser Val Ala Pro Gly Lys
1               5                   10                  15

Thr Ala Ser Leu Thr Cys Gly Tyr Asn Ile Gly Thr Lys Ser Val His
            20                  25                  30

Trp Tyr Gln Gln Lys Pro Gly Gln Ala Pro Val Val Val Val His Asp
        35                  40                  45

Asp Ser Asp Arg Pro Ser Gly Ile Pro Glu Arg Phe Ser Gly Ser Asn
    50                  55                  60

Ser Gly Thr Thr Ala Thr Leu Thr Ile Ser Arg Val Glu Ala Gly Asp
65                  70                  75                  80

Glu Ala Asp Tyr Tyr Cys Gln Ala Trp Asp Ser Ile Ser Glu Glu Val
                85                  90                  95

Val Phe Gly Gly Gly Thr Lys Leu Thr Val
            100                 105

<210> SEQ ID NO 49
<211> LENGTH: 21
<212> TYPE: PRT
<213> ORGANISM: Artificial Sequence
<220> FEATURE:
<223> OTHER INFORMATION: Synthetic Construct

<400> SEQUENCE: 49

Ser Glu Leu Thr Gln Asp Pro Ala Val Ser Val Ala Leu Gly Gln Thr
1               5                   10                  15

Val Arg Ile Thr Cys
```

```
                          20

<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Gln Gly Asp Ser Leu Arg Ser Tyr Tyr Ala Ser
  1               5                  10

<210> SEQ ID NO 51
<211> LENGTH: 14
<212> TYPE: PRT
<213> ORGANISM: Artificial Sequence
<220> FEATURE:
<223> OTHER INFORMATION: Synthetic Construct

<400> SEQUENCE: 51

Trp Tyr Gln Gln Lys Pro Gly Gln Ala Pro Val Leu Val Ile
  1               5                  10

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Tyr Gly Lys Asn Lys Arg Pro Ser
  1               5

<210> SEQ ID NO 53
<211> LENGTH: 32
<212> TYPE: PRT
<213> ORGANISM: Artificial Sequence
<220> FEATURE:
<223> OTHER INFORMATION: Synthetic Construct

<400> SEQUENCE: 53

Gly Ile Pro Asp Arg Phe Ser Gly Ser Ser Gly Asn Thr Ala Ser
  1               5                  10                  15

Leu Thr Ile Thr Gly Ala Gln Ala Val Asp Glu Ala Asp Tyr His Cys
                 20                  25                  30

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Asn Ser Arg Asp Ser Ser Gly Asn His Val Val
  1               5                  10

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55
```

```
Phe Gly Gly Gly Thr Lys Leu Thr Val
 1               5

<210> SEQ ID NO 56
<211> LENGTH: 106
<212> TYPE: PRT
<213> ORGANISM: Artificial Sequence
<220> FEATURE:
<223> OTHER INFORMATION: Synthetic Construct

<400> SEQUENCE: 56

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
             20                  25                  30

Trp Tyr Gln Gln Lys Pro Gly Gln Ala Pro Val Leu Val Ile Tyr Gly
         35                  40                  45

Lys Asn Lys Arg Pro Ser Gly Ile Pro Asp Arg Phe Ser Gly Ser Ser
     50                  55                  60

Ser Gly Asn Thr Ala Ser Leu Thr Ile Thr Gly Ala Gln Ala Val Asp
 65                  70                  75                  80

Glu Ala Asp Tyr His Cys Asn Ser Arg Asp Ser Ser Gly Asn His Val
                 85                  90                  95

Val Phe Gly Gly Gly Thr Lys Leu Thr Val
                100                 105

<210> SEQ ID NO 57
<211> LENGTH: 22
<212> TYPE: PRT
<213> ORGANISM: Artificial Sequence
<220> FEATURE:
<223> OTHER INFORMATION: Synthetic Construct

<400> SEQUENCE: 57

Asn Phe Met Leu Thr Gln Pro Pro Ser Val Ser Val Ala Pro Gly Lys
 1               5                  10                  15

Thr Ala Ser Leu Thr Cys
             20

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Gly Gly Tyr Asn Ile Gly Thr Lys Ser Val His
 1               5                  10

<210> SEQ ID NO 59
<211> LENGTH: 14
<212> TYPE: PRT
<213> ORGANISM: Artificial Sequence
<220> FEATURE:
<223> OTHER INFORMATION: Synthetic Construct

<400> SEQUENCE: 59

Trp Tyr Gln Gln Lys Pro Gly Gln Ala Pro Val Val Val Val
 1               5                  10

<210> SEQ ID NO 60
```

<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

His Asp Asp Ser Asp Arg Pro Ser
1               5

<210> SEQ ID NO 61
<211> LENGTH: 32
<212> TYPE: PRT
<213> ORGANISM: Artificial Sequence
<220> FEATURE:
<223> OTHER INFORMATION: Synthetic Construct

<400> SEQUENCE: 61

Gly Ile Pro Glu Arg Phe Ser Gly Ser Asn Ser Gly Thr Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Gln Ala Trp Asp Ser Ile Ser Glu Glu Val Val
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Phe Gly Gly Gly Thr Lys Leu Thr Val
1               5

<210> SEQ ID NO 64
<211> LENGTH: 107
<212> TYPE: PRT
<213> ORGANISM: Artificial Sequence
<220> FEATURE:
<223> OTHER INFORMATION: Synthetic Construct

<400> SEQUENCE: 64

Asn Phe Met Leu Thr Gln Pro Pro Ser Val Ser Val Ala Pro Gly Lys
1               5                   10                  15

Thr Ala Ser Leu Thr Cys Gly Gly Tyr Asn Ile Gly Thr Lys Ser Val
            20                  25                  30

His Trp Tyr Gln Gln Lys Pro Gly Gln Ala Pro Val Val Val Val His
        35                  40                  45

Asp Asp Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Ala Trp Asp Ser Ile Ser Glu Glu

```
                    85                  90                  95
Val Val Phe Gly Gly Gly Thr Lys Leu Thr Val
                100                 105

<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65

Gly Gly Gly Gly Ser Gly Gly Gly Gly Ser Gly Gly Gly Gly Ser
1               5                   10                  15

<210> SEQ ID NO 66
<211> LENGTH: 30
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 67
<211> LENGTH: 5
<212> TYPE: PRT
<213> ORGANISM: Artificial Sequence
<220> FEATURE:
<223> OTHER INFORMATION: Synthetic Construct

<400> SEQUENCE: 67

Ser Tyr Ala Leu Ser
1               5

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

Trp Val Arg Gln Ala Pro Gly Lys Gly Leu Glu Trp Val Ser
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Synthetic Construct

<400> SEQUENCE: 69

Ala Ile Ser Gly Ser Gly Gly Ser Thr Tyr Tyr Ala Gly Ser Val Lys
1               5                   10                  15

Gly

<210> SEQ ID NO 70
<211> LENGTH: 32
<212> TYPE: PRT
```

```
<213> ORGANISM: Artificial Sequence
<220> FEATURE:
<223> OTHER INFORMATION: Synthetic Construct

<400> SEQUENCE: 70

Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Lys
             20                  25                  30

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct

<400> SEQUENCE: 71

Gly Leu Ile Ala Ser His
 1               5

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Trp Gly Gln Gly Thr Leu Val Thr Val Ser Ser
 1               5                  10

<210> SEQ ID NO 73
<211> LENGTH: 115
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Leu Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Gly Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Leu Ile Ala Ser His Trp Gly Gln Gly Thr Leu Val Thr
            100                 105                 110

Val Ser Ser
        115

<210> SEQ ID NO 74
<211> LENGTH: 21
<212> TYPE: PRT
<213> ORGANISM: Artificial Sequence
<220> FEATURE:
<223> OTHER INFORMATION: Synthetic Construct
```

<400> SEQUENCE: 74

Ser Glu Leu Thr Gln Asp Pro Ala Val Ser Val Ala Leu Gly Gln Thr
1               5                   10                  15

Val Arg Ile Thr Cys
            20

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Gln Gly Asp Ser Leu Arg Ser Tyr Tyr Ala Ser
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

Trp Tyr Gln Gln Lys Pro Gly Gln Ala Pro Val Leu Val Ile
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Tyr Gly Lys Asn Asn Arg Pro Ser
1               5

<210> SEQ ID NO 78
<211> LENGTH: 32
<212> TYPE: PRT
<213> ORGANISM: Artificial Sequence
<220> FEATURE:
<223> OTHER INFORMATION: Synthetic Construct

<400> SEQUENCE: 78

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Asn Ser Arg Asp Ser Ser Gly Ile His Leu Val
1               5                   10

<210> SEQ ID NO 80

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 80

Phe Gly Gly Gly Thr Lys Leu Thr Val Leu
 1               5                  10

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
                20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Ile His Leu
                85                  90                  95

Val Phe Gly Gly Gly Thr Lys Leu Thr Val Leu
                100                 105
```